US009868715B2

(12) United States Patent
Zhou et al.

(10) Patent No.: US 9,868,715 B2
(45) Date of Patent: Jan. 16, 2018

(54) APIGENIN ANALOGS, COMPOSITIONS, AND METHODS RELATED THERETO

(71) Applicants: Jia Zhou, League City, TX (US); Mark Hellmich, Galveston, TX (US); Csaba Szabo, Seattle, WA (US)

(72) Inventors: Jia Zhou, League City, TX (US); Mark Hellmich, Galveston, TX (US); Csaba Szabo, Seattle, WA (US)

(73) Assignee: THE BOARD OF REGENTS OF THE UNIVERSITY OF TEXAS SYSTEMS, Austin, TX (US)

( * ) Notice: Subject to any disclaimer, the term of this patent is extended or adjusted under 35 U.S.C. 154(b) by 0 days.

(21) Appl. No.: 15/304,966

(22) PCT Filed: Apr. 18, 2015

(86) PCT No.: PCT/US2015/026563
§ 371 (c)(1),
(2) Date: Oct. 18, 2016

(87) PCT Pub. No.: WO2015/161309
PCT Pub. Date: Oct. 22, 2015

(65) Prior Publication Data
US 2017/0204078 A1    Jul. 20, 2017

Related U.S. Application Data

(60) Provisional application No. 61/981,785, filed on Apr. 19, 2014.

(51) Int. Cl.
*C07D 311/30* (2006.01)
*C07D 405/12* (2006.01)
*C07D 407/12* (2006.01)

(52) U.S. Cl.
CPC .......... *C07D 311/30* (2013.01); *C07D 405/12* (2013.01); *C07D 407/12* (2013.01)

(58) Field of Classification Search
CPC .................................................. C07D 311/30
USPC ....................................................... 549/462
See application file for complete search history.

(56) References Cited

U.S. PATENT DOCUMENTS 6,239,114 B1 * 5/2001 Guthrie ................ A61K 31/352
514/32
2009/0269793 A1 * 10/2009 Mely ..................... C07D 409/04
435/29

OTHER PUBLICATIONS

Aghdassi et al. 2011, Fibrogenesis Tissue Repair 4:26.
Asimakopoulou et al. 2013, Br J Pharmacol. 169(4):922-32.
Chan et al., "Flavonoid dimers as bivalent modulators for P-glycoprotein-based multidrug resistance: synthetic apigenin homodimers linked with defined-length poly(ethylene glycol) spacers increase drug retention and enhance chemosensitivity in resistant cancer cells." J Med Chem, vol. 49, No. 23, 2006, pp. 6742-6759.
Chan et al., "Flavonoid dimers as bivalent modulators for p-glycoprotein-based multidrug resistance: structure-activity relationships." ChemMedChem, vol. 4, No. 4, 2009, pp. 594-614.
Chao et al., "Gastrointestinal hormone receptors in primary human colorectal carcinomas." J Surg Res, vol. 129, No. 2, 2005, pp. 313-321.
Chen et al., 2013, ACS Med Chem Lett 4:180.
Erkan et al., 2012, Gut 61:172.
Everhart et al., "Burden of digestive diseases in the United States part I: overall and upper gastrointestinal diseases." Gastroenterology, vol. 136, No. 2, 2009, pp. 376-386.
Forsmark, "Management of Chronic Pancreatitis." Gastroenterology, vol. 144, No. 6, 2013, pp. 1282-1291.
Gao et al., 2013, Am J Physiol Gastrointest Liver Physiol 304:G804.
Gradolatto et al., 2004, Drug Metab Dispos 32:58.
Gradolatto et al., 2005, Drug Metab Dispos 33:49.
Harvey, "Natural products in drug discovery." Drug Discov Today, vol. 13, No. 19, 2008, pp. 894-901.
He et al., "Protection of cerulein-induced pancreatic fibrosis by pancreas-specific expression of Smad7." Biochim Biophys Acta, vol. 1792, No. 1, 2009, pp. 56-60.
International Preliminary Report on Patentability in International Application No. PCT/US2015/026563, dated Nov. 3, 2016.
International Search Report and Written Opinion in International Application No. PCT/US2015/026563, dated Aug. 21, 2015.
Jaster et al., "Crucial role of fibrogenesis in pancreatic diseases." J Best Pract Res Clin Gastroenterol, vol. 22, No. 1, 2008, pp. 17-29.
Keller et al., "A practical view of 'druggability'." Curr Opin Chem Biol, vol. 10, No. 4, 2006, pp. 357-361.
Klöoppel et al., "Pathology of acute and chronic pancreatitis." Pancreas, vol. 8, No. 6, 1993, pp. 659-670.
Koehn et al., "The evolving role of natural products in drug discovery." Nat Rev Drug Discov, vol. 4, No. 3, 2005, pp. 206-220.
Lerch et al., "Models of acute and chronic pancreatitis." Gastroenterology, vol. 144, No. 6, 2013, pp. 1180-1193.
Lin et al., 2007, J Med Chem 50:3921.
Manthey et al., "Antiproliferative activities of citrus flavonoids against six human cancer cell lines." J Agric Food Chem, vol. 50, No. 21, 2002, pp. 5837-5843.
Masamune et al., "Roles of pancreatic stellate cells in pancreatic inflammation and fibrosis." Clin Gastroenterol Hepatol, vol. 7, No. 11, pp. S48-S54.
Pubchem Compound Summary for CID 66784171 dated Jul. 31, 2015.

(Continued)

*Primary Examiner* — Taofiq A Solola
(74) *Attorney, Agent, or Firm* — Norton Rose Fulbright US LLP

(57) ABSTRACT

Certain embodiments are directed to apigenin analogues or derivatives. In certain aspects, the derivatives are developed as cystathionine-beta-synthase (CBS) inhibitors. In certain aspects, the derivatives are used as anticancer or anti-inflammatory agents. Certain embodiments are directed methods of treating or compositions used to treat fibrosis and cancers. In certain aspects one or more compounds described herein can be administered to a subject to treat pancreatic fibrosis, liver fibrosis, pancreatic cancer, colon cancer, breast cancer, brain tumors, head/neck cancer, prostate and lung cancers as well as other inflammation.

6 Claims, 3 Drawing Sheets

(56) References Cited

OTHER PUBLICATIONS

Pubchem Substance Record for SID 105150778 dated Jul. 31, 2015.
Sahel et al., "Modifications of pure human pancreatic juice induced by chronic alcohol consumption." Dig Dis Sci, vol. 24, No. 12, 1979, pp. 897-905.
Schneider et al., "Hereditary pancreatitis: a model for inflammatory diseases of the pancreas." Best Pract Res Clin Gastroenterol, vol. 16, No. 3, 2002, pp. 347-363.
Shimizu, "Mechanisms of pancreatic fibrosis and applications to the treatment of chronic pancreatitis." Gastroenterol, vol. 43, No. 11, 2008, pp. 823-832.
Shukla et al., 2010, Pharm Res 27:962.
Spector et al., "Inhibition of pancreatic stellate cell activation by halofuginone prevents pancreatic xenograft tumor development." Pancreas, vol. 39, No. 7, 2010, pp. 1008-1015.
Trikudanathan et al., "Modern treatment of patients with chronic pancreatitis." Gastroenterol Clin North Am, vol. 41, No. 1, 2012, pp. 63-76.
Walle, "Methylation of dietary flavones greatly improves their hepatic metabolic stability and intestinal absorption." Mol Pharm, vol. 4, No. 6, 2007, pp. 826-832.
Wen et al., 2006, Drug Metab Dispos 34:1786.
Whitcomb, 1999, Gut 45:317.
Witt et al., "Chronic pancreatitis: challenges and advances in pathogenesis, genetics, diagnosis, and therapy." Gastroenterology, vol. 132, No. 4, 2007, pp. 1557-1573.
Yang et al., "Epidemiology of alcohol-related liver and pancreatic disease in the United States." Arch Intern Med, vol. 168, No. 6, 2008, pp. 649-656.

\* cited by examiner

APIGENIN ANALOGS, COMPOSITIONS, AND METHODS RELATED THERETO

This application is a national phase application under 35 U.S.C. § 371 of International Application No. PCT/US2015/026563, filed Apr. 18, 2015 which claims priority to U.S. Provisional Patent Application 61/981,785, filed Apr. 19, 2014 Both applications are hereby incorporated in their entirety.

STATEMENT REGARDING FEDERALLY FUNDED RESEARCH

This invention was made with government support under P50 CA097007, P30 DA028821, R21 MH093844, T32 DK007639-21, and K08 CA125209 awarded by the National Institutes of Health. The government has certain rights in the invention.

BACKGROUND

Certain embodiments are directed to the fields of chemistry and medicine. Certain aspects are directed to compounds for treating chronic pancreatitis, colon cancer, or liver fibrosis.

Chronic pancreatitis (CP) is a progressive, non-curable disorder of the pancreas (Schneider and Whitcomb, 2002, Best Pract Res Clin Gastroenterol 16:347). Pathologically, both the endocrine and exocrine pancreas undergo progressive and often irreversible morphological changes, including glandular fibrosis (Bordalo et al. 1977, Am J Gastroenterol 68:278; Shimizu 2008, Gastroenterol 43:823; Sahel and Sarles 1979, Dig Dis Sci 24:897; Witt et al. 2007, Gastroenterology 132:15570). In the United States, disorders of the exocrine pancreas affect over 1 million patients and result in a cost of over $3.7 billion annually (Yang et al. 2008, Arch Intern Med 168:649; Everhart and Ruhl 2009, Gastroenterology 136:376). Current treatment options for CP are limited to supportive and palliative care; patients with advanced disease can be managed with endoscopic and/or surgical pancreatic decompression, denervation, resection, bypass, or transplantation (Trikudanathan et al. 2012, Gastroenterol Clin North Am 41:63; Forsmark 2013, Gastroenterology 144:1282). Overall, patients have a poor quality of life, and are burdened by chronic abdominal pain, increased hospitalizations, impaired digestion, diarrhea, weight loss, diabetes, complications like pseudocysts and an increased risk of pancreatic cancer (Forsmark 2013, Gastroenterology 144:1282). Therefore, the development of effective, safe and affordable therapeutic agents remains a critical need.

SUMMARY

Classes of small molecules can be developed as highly potent and orally active agents for the prevention and treatment of various fibrosis and cancers including but not limited to pancreatic fibrosis, liver fibrosis, pancreatic cancer, colon cancer, breast cancer, brain tumors, head/neck cancer, prostate and lung cancers as well as other inflammation. These molecules may also be useful research tools and therapeutics as cystathionine-β-synthase (CBS) inhibitors to target H$_2$S-signaling for a wide range of human diseases.

Accumulating evidence suggests that activated pancreatic stellate cells (PSC) play an important role in chronic pancreatitis (CP), and inhibition of the activated PSC is considered as a potential strategy for the treatment and prevention of CP. Herein, the inventors disclose findings that apigenin and its novel analogues suppress the proliferation and induce apoptosis in PSC which reduce the PSC-mediated fibrosis in CP. Chemical modifications of apigenin have been directed to build a focused library of O-alkylamino-tethered apigenin derivatives at 4'-O position of the ring C with the attempt to enhance the potency and drug-like properties including aqueous solubility. A number of compounds such as 14 (HJC-5-56), 16 (HJC-5-57), and 24 (HJC-5-100) exhibited potent antiproliferative effects as well as improved aqueous solubility. Intriguingly, apigenin, new analogues 23 (HJC-5-61) and 24 (HJC-5-100) displayed significant efficacy to reduce pancreatic fibrosis even at a low dose of 0.5 mg/kg in our proof-of-concept study using a preclinical in vivo mouse model of CP.

Certain embodiments are directed to compounds having the general formula of Formula I:

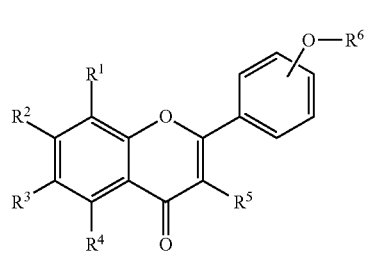

Formula I where $R^1$, $R^2$, $R^3$, $R^4$, and $R^5$, are independently hydrogen, methoxy, hydroxy, oxo, nitro, halo, mercapto, cyano, azido, amino, imino, azo, sulfonyl, sulfinyl, sulfo, thioyl, methyl, ethyl, C1-C6 alkoxy, C1-C6 hydroxyalkyl, C1-C6 carboxylate, C1-C6 carboxyl, C2-C4 carbonyl, C2-C4 aldehyde, C2-C8 heteroalkyl, C1-C6 alkylsulfonyl, C1-C6 alkylhalide; and $R^6$ is oxo, nitro, halo, mercapto, cyano, azido, amino, imino, azo, —C(NH)(NH$_2$), sulfonyl, sulfinyl, sulfo, thioyl, methyl, ethyl, C2-C6 alkyl, C1-C6 alkoxy, C1-C6 alkylamine, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1-C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl.

In certain aspects $R^1$, $R^3$, and $R^5$ are hydrogen. In still a further aspect $R^2$ and $R^4$ are independently C1-C4 alkoxy. In certain aspects $R^2$ and $R^4$ are methoxy.

In certain aspects $R^6$ is a 5 or 6 member heterocycle. In a further embodiment $R^6$ is a nitrogen containing heterocycle. In still a further aspect $R^6$ is a substituted or unsubstituted pyrrolidine or piperidine.

In certain embodiments $R^6$ is a 3 member heterocycle. In a further embodiment $R^6$ is oxygen containing heterocycle. In still further aspects $R^6$ is an epoxide.

In certain aspects the compound is selected from 2-(4-Hydroxy-phenyl)-5,7-dimethoxy-chromen-4-one (HJC-5-14), 2-[4-(2-Bromo-ethoxy)-phenyl]-5,7-dimethoxy-chromen-4-one (HJC-5-51), 2-[4-(2-Fluoro-ethoxy)-phenyl]-5,7-dimethoxy-chromen-4-one (HJC-5-54), 5,7-Dimethoxy-2-[4-(1-methyl-piperidin-4-yloxy)-phenyl]-chromen-4-one (HJC-5-38), 2-[4-(2-Dimethylamino-ethoxy)-phenyl]-5,7-dimethoxy-chromen-4-one (HJC-5-15), 5,7-Dimethoxy-2-[4-(2-morpholin-4-yl-ethoxy)-phenyl]-chromen-4-one (HJC-5-16), 2-[4-(3-Dimethylamino-propoxy)-phenyl]-5,7-dimethoxychromen-4-one (HJC-5-74), 1-{2-[4-(5,7-Dimethoxy-4-oxo-4H-chromen-2-yl)-phenoxy]-ethyl}-pyrrolidin-2-one (HJC-5-76), 5,7-Dimethoxy-2-[4-(2-piperidin-1-yl-ethoxy)-phenyl]-chromen-4-one (HJC-5-56), 5,7-Dimethoxy-2-{4-[2-(4-methyl-piperazin-1-yl)-ethoxy]-phenyl}-chromen-4-one (HJC-5-53), 5,7-Dimethoxy-2-[4-(2-pyrrolidin-1-yl-ethoxy)-phenyl]-chromen-4-one (HJC-5-57), 2-[4-(2-Diethylamino-ethoxy)-phenyl]-5,7-dimethoxy-chromen-4-one (HJC-5-81), 1-{2-[4-(5,7-Dimethoxy-4-oxo-4H-chromen-2-yl)-phenoxy]-ethyl}-pyrrolidine-2-carboxylic acid methyl ester (HJC-5-80), 5,7-Dimethoxy-2-[4-(piperidin-4-yloxy)-phenyl]-chromen-4-one (HJC-5-43), 2-[4-(2-Amino-ethoxy)-phenyl]-5,7-dimethoxy-chromen-4-one (HJC-5-18), 2-[4-(3-Amino-propoxy)-phenyl]-5,7-dimethoxy-chromen-4-one (HJC-5-42), 5,7-Dimethoxy-2-(4-oxiranylmethoxy-phenyl)-chromen-4-one (HJC-5-61), 2-[4-(2-Hydroxy-3-piperidin-1-yl-propoxy)-phenyl]-5,7-dimethoxy-chromen-4-one (HJC-5-100), 2-[4-(2-Hydroxy-3-pyrrolidin-1-yl-propoxy)-phenyl]-5,7-dimethoxy-chromen-4-one (HJC-6-4), 2-[4-(3-Dimethylamino-2-hydroxy-propoxy)-phenyl]-5,7-dimethoxy-chromen-4-one (HJC-5-65), 2-[4-(2,3-Dihydroxy-propoxy)-phenyl]-5,7-dimethoxy-chromen-4-one (HJC-5-99), 2-(4-Bromo-phenyl)-5,7-dimethoxy-chromen-4-one (HJC-5-78), 2-[4-(6-Fluoro-pyridin-3-yl)-phenyl]-5,7-dimethoxy-chromen-4-one (HJC-6-7), 2-[4-(2-Dimethylamino-ethylamino)-phenyl]-5,7-dimethoxy-chromen-4-one (HJC-6-11), 5,7-Dimethoxy-2-[4-(2-pyrrolidin-1-yl-ethylamino)-phenyl]-chromen-4-one (HJC-6-23), 5-Hydroxy-7-methoxy-2-[4-(2-pyrrolidin-1-yl-ethoxy)-phenyl]-chromen-4-one (HJC-5-97), and 5,7-Dihydroxy-2-[4-(2-pyrrolidin-1-yl-ethoxy)-phenyl]-chromen-4-one (HJC-6-1)

Certain embodiments are directed to compounds having the general formula of Formula II:

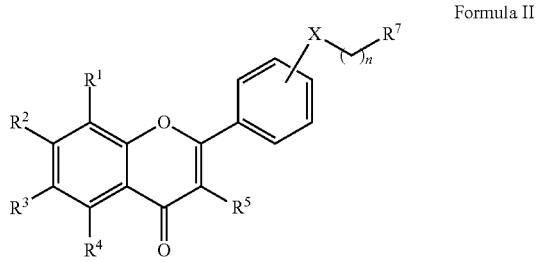

Formula II where X=O, N, S, or C; n=0, 1, 2, 3, 4, or 5; $R^1$, $R^2$, $R^3$, $R^4$, and $R^5$ are as described above; and $R^7$ is hydroxy, oxo, nitro, halo, mercapto, cyano, azido, amino, imino, azo, —C(NH)(NH$_2$), sulfonyl, sulfinyl, sulfo, thioyl, methyl, ethyl, aminooxy, C2-C6 alkyl, C1-C6 alkoxy, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1-C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl.

In certain aspects X is O or N. In a further aspects n is 2. In certain aspects $R^1$, $R^3$, and $R^5$ are hydrogen. In still a further aspect $R^2$ and $R^4$ are independently C1-C4 alkoxy. In certain aspects $R^2$ and $R^4$ are methoxy. In certain aspects X is at the 4' position.

In certain aspects $R^7$ is a 5 or 6 member heterocycle. In a further embodiment $R^7$ is a nitrogen containing heterocycle. In still a further aspect $R^7$ is a substituted or unsubstituted pyrrolidine or piperidine.

In certain embodiments $R^7$ is a 3 member heterocycle. In a further embodiment $R^7$ is oxygen containing heterocycle. In still further aspects $R^7$ is an epoxide.

In certain aspects a compound of Formula II is 2-[4-(2-Bromo-ethoxy)-phenyl]-5,7-dimethoxy-chromen-4-one (HJC-5-51), 2-[4-(2-Fluoro-ethoxy)-phenyl]-5,7-dimethoxy-chromen-4-one (HJC-5-54), 5,7-Dimethoxy-2-[4-(1-methyl-piperidin-4-yloxy)-phenyl]-chromen-4-one (HJC-5-38), 2-[4-(2-Dimethylamino-ethoxy)-phenyl]-5,7-dimethoxy-chromen-4-one (HJC-5-15), 5,7-Dimethoxy-2-[4-(2-morpholin-4-yl-ethoxy)-phenyl]-chromen-4-one (HJC-5-16), 2-[4-(3-Dimethylamino-propoxy)-phenyl]-5,7-dimethoxy-chromen-4-one (HJC-5-74), 1-{2-[4-(5,7-Dimethoxy-4-oxo-4H-chromen-2-yl)-phenoxy]-ethyl}-pyrrolidin-2-one (HJC-5-76), 5,7-Dimethoxy-2-[4-(2-piperidin-1-yl-ethoxy)-phenyl]-chromen-4-one (HJC-5-56), 5,7-Dimethoxy-2-{4-[2-(4-methyl-piperazin-1-yl)-ethoxy]-phenyl}-chromen-4-one (HJC-5-53), 5,7-Dimethoxy-2-[4-(2-pyrrolidin-1-yl-ethoxy)-phenyl]-chromen-4-one (HJC-5-57), 2-[4-(2-Diethylamino-ethoxy)-phenyl]-5,7-dimethoxy-chromen-4-one (HJC-5-81), 1-{2-[4-(5,7-Dimethoxy-4-oxo-4H-chromen-2-yl)-phenoxy]-ethyl}-pyrrolidine-2-carboxylic acid methyl ester (HJC-5-80), 5,7-Dimethoxy-2-[4-(piperidin-4-yloxy)-phenyl]-chromen-4-one (HJC-5-43), 2-[4-(2-Amino-ethoxy)-phenyl]-5,7-dimethoxy-chromen-4-one (HJC-5-18), 2-[4-(3-Amino-propoxy)-phenyl]-5,7-dimethoxy-chromen-4-one (HJC-5-42), 5,7-Dimethoxy-2-(4-oxiranylmethoxy-phenyl)-chromen-4-one (HJC-5-61), 2-[4-(2-Hydroxy-3-piperidin-1-yl-propoxy)-phenyl]-5,7-dimethoxy-chromen-4-one (HJC-5-100), 2-[4-(2-Hydroxy-3-pyrrolidin-1-yl-propoxy)-phenyl]-5,7-dimethoxy-chromen-4-one (HJC-6-4), 2-[4-(3-Dimethylamino-2-hydroxy-propoxy)-phenyl]-5,7-dimethoxy-chromen-4-one (HJC-5-65), 2-[4-(2,3-Dihydroxy-propoxy)-phenyl]-5,7-dimethoxy-chromen-4-one (HJC-5-99), 2-[4-(6-Fluoro-pyridin-3-yl)-phenyl]-5,7-dimethoxy-chromen-4-one (HJC-6-7), 2-[4-(2-Dimethylamino-ethylamino)-phenyl]-5,7-dimethoxy-chromen-4-one (HJC-6-11), 5,7-Dimethoxy-2-[4-(2-pyrrolidin-1-yl-ethylamino)-phenyl]-chromen-4-one (HJC-6-23), 5-Hydroxy-7-methoxy-2-[4-(2-pyrrolidin-1-yl-ethoxy)-phenyl]-chromen-4-one (HJC-5-97), or 5,7-Dihydroxy-2-[4-(2-pyrrolidin-1-yl-ethoxy)-phenyl]-chromen-4-one (HJC-6-1).

Certain aspects are directed to a compound having the formula of Formula VII.

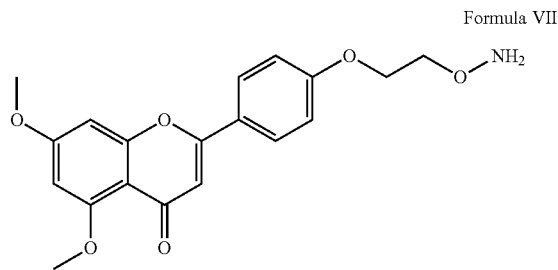 [SMILES: COc1cc(OC)c2c(=O)cc(-c3ccc(OCCON)cc3)oc2c1]

Formula VII

Certain embodiments are directed to compounds having the general formula of Formula III:

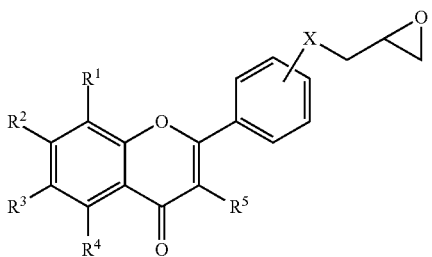

Formula III where X=O, N, S, or C; $R^1$, $R^2$, $R^3$, $R^4$, and $R^5$ are independently hydrogen, oxo, nitro, halo, mercapto, cyano, azido, amino, imino, azo, —C(NH)(NH$_2$), sulfonyl, sulfinyl, sulfo, thioyl, methyl, ethyl, C2-C6 alkyl, C1-C6 alkoxy, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1-C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl.

In certain aspects X is O. In a further aspect $R^1$, $R^3$, and $R^5$ are hydrogen. In still a further aspect $R^2$ and $R^4$ are independently C1-C4 alkoxy. In certain aspects $R^2$ and $R^4$ are methoxy. In certain aspects X is at the 4' position.

In certain aspects the compound is 5,7-Dimethoxy-2-(4-oxiranylmethoxy-phenyl)-chromen-4-one Certain embodiments are directed to compounds having the general formula of Formula IV:

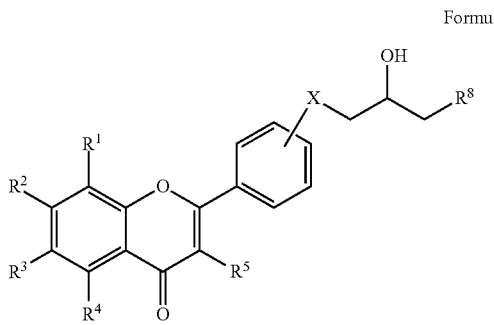

Formula IV where X=O, N, S, or C; $R^1$, $R^2$, $R^3$, $R^4$, and $R^5$ are as described above; and $R^8$ is hydroxy, oxo, nitro, halo, mercapto, cyano, azido, amino, imino, azo, —C(NH)(NH$_2$), sulfonyl, sulfinyl, sulfo, thioyl, methyl, ethyl, C2-C6 alkyl, C1-C6 alkoxy, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1-C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl. In certain aspects, $R^1$ and $R^2$ can optionally form a substituted or unsubstituted 3 to 8 membered heterocycle or 3 to 9 membered cycloalkyl.

In certain aspects $R^1$, $R^3$, and $R^5$ are hydrogen. In still a further aspect $R^2$ and $R^4$ are independently C1-C4 alkoxy. In certain aspects $R^2$ and $R^4$ are methoxy. In certain aspects X is at the 4' position.

In certain aspects $R^8$ is a 5 or 6 member heterocycle. In a further embodiment $R^8$ is a nitrogen containing heterocycle. In still a further aspect $R^8$ is a substituted or unsubstituted pyrrolidine or piperidine.

In certain embodiments $R^8$ is a 3, 4, 5, or 6 member heterocycle. In a further embodiment $R^8$ is oxygen containing heterocycle. In still further aspects $R^8$ is an epoxide.

In certain aspects a compound of Formula IV is selected from 2-[4-(2-Hydroxy-3-piperidin-1-yl-propoxy)-phenyl]-5,7-dimethoxy-chromen-4-one (HJC-5-100), 2-[4-(2-Hydroxy-3-pyrrolidin-1-yl-propoxy)-phenyl]-5,7-dimethoxy-chromen-4-one (HJC-6-4), 2-[4-(3-Dimethylamino-2-hydroxy-propoxy)-phenyl]-5,7-dimethoxy-chromen-4-one (HJC-5-65), and 2-[4-(2,3-Dihydroxy-propoxy)-phenyl]-5,7-dimethoxy-chromen-4-one (HJC-5-99).

Certain embodiments are directed to compounds having the general formula of Formula V:

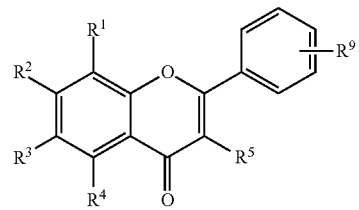

Formula V where $R^1$, $R^2$, $R^3$, $R^4$, and $R^5$ are as described above; and $R^9$ is hydroxy, oxo, nitro, halo, mercapto, cyano, azido, amino, imino, azo, —C(NH)(NH$_2$), sulfonyl, sulfinyl, sulfo, thioyl, methyl, ethyl, C2-C6 alkyl, C1-C6 alkoxy, C1-C6 alkylamine, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1-C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl, wherein R9 is not a 4' hydroxy if $R^1$, $R^3$, and $R^5$ are hydrogen and $R^2$, and $R^4$ are hydroxy.

In certain aspects $R^1$, $R^3$, and $R^5$ are hydrogen. In still a further aspect $R^2$ and $R^4$ are independently C1-C4 alkoxy. In certain aspects $R^2$ and $R^4$ are methoxy. In certain aspects $R^9$ is at the 4' position.

Certain embodiments are directed to compounds having the general formula of Formula I:

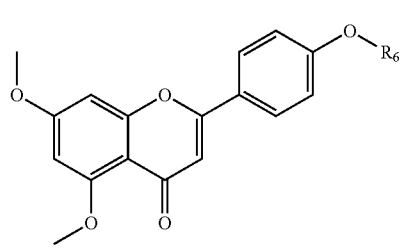

Formula VI

Wherein $R^6$ is oxo, nitro, halo, mercapto, cyano, azido, amino, imino, azo, —C(NH)(NH$_2$), sulfonyl, sulfinyl, sulfo, thioyl, methyl, ethyl, C2-C6 alkyl, C1-C6 alkoxy, C1-C6 alkylamine, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1-C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl.

Certain embodiments are directed methods of treating or compositions used to treat fibrosis and cancers. In certain aspects one or more compounds described herein can be administered to a subject to treat pancreatic fibrosis, liver fibrosis, pancreatic cancer, colon cancer, breast cancer, brain tumors, head/neck cancer, prostate and lung cancers as well as other inflammation. In certain aspects methods of treating are directed to pancreatic fibrosis, liver fibrosis, or colon cancer.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The use of the word "a" or "an" when used in conjunction with the term "comprising" in the claims and/or the specification may mean "one," but it is also consistent with the meaning of "one or more," "at least one," and "one or more than one."

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
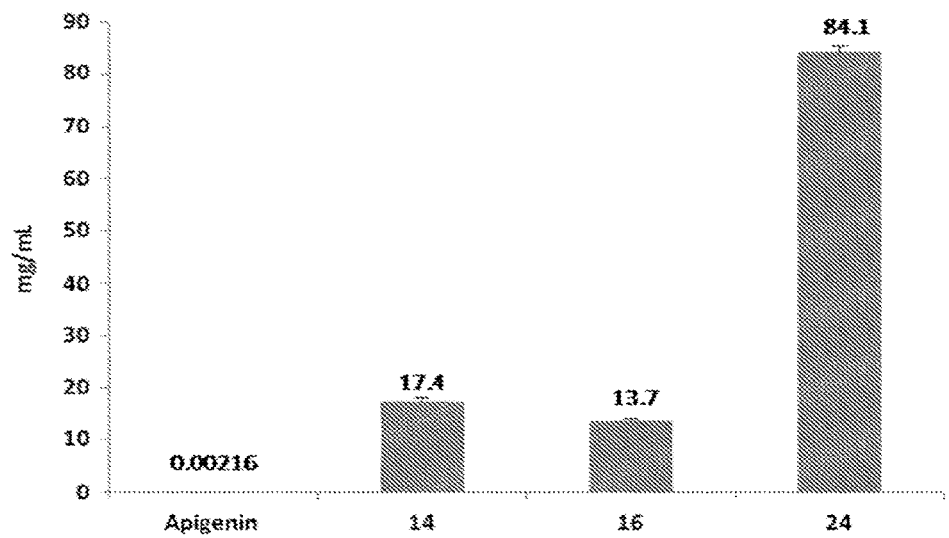
FIG. 1. Aqueous solubility of apigenin and selected apigenin derivatives. Compounds 14, 16 and 24 (in the form of HCl salt) showed significantly improved solubility as compared with apigenin.

Within the last two decades, it has been well-established that pancreatic stellate cells (PSC) are responsible for the fibrotic component of chronic pancreatitis (CP), and suppressing PSC is therefore a potential therapeutic target for the disease (Erkan et al. 2008, *Gut* 61:172; Jaster and Emmrich 2008, J. *Best Pract Res Clin Gastroenterol* 22:17; Masamune et al. 2009, *Clin Gastroenterol Hepatol* 7:S48). In the normal pancreas, PSC are inactive/quiescent, whereas during tissue injury, PSC display an activated, myofibroblastic phenotype, with increased proliferation, motility, and secretion of extracellular matrix proteins (Erkan et al. 2008, *Gut* 61:172; Jaster and Emmrich 2008, J. *Best Pract Res Clin Gastroenterol* 22:17; Masamune et al. 2009, *Clin Gastroenterol Hepatol* 7:S48). CP favors the perpetual activation of PSC (Madro et al. 2011 *Adv Med Sci* 56:132). Consequently, a promising strategy for the prevention and treatment of CP involves limiting the proliferation and inducing apoptosis of activated PSC (Madro et al. 2011, *Adv Med Sci* 56:132; Gao et al. 2013, *Am J Physiol Gastrointest Liver Physiol* 304: G804; Spector et al. 2010, *Pancreas* 39:1008; He et al. 2009, *Biochim Biophys Acta* 1792:56).

The sentinel acute pancreatitis event (SAPE) hypothesis provides a unified model for the pathogenesis of CP (Whitcomb 1999, *Gut* 45:317). After studying cases of hereditary pancreatitis, Whitcomb et al. found that 50% of patients with gain-of-function trypsinogen mutations experienced repeated episodes of acute pancreatitis (AP) that later developed into CP (Schneider and Whitcomb 2002, *Best Pract Res Clin Gastroenterol* 16:347; Whitcomb 1999, *Gut* 45:317). Regardless of the inciting etiology(s) of the sentinel event of AP, recurrent episodes of AP cause CP. AP is initiated with acinar cell injury, characterized by premature acinar zymogen activation, recruitment of inflammatory cells, auto-digestion and necrosis of acinar and ductal cells, subsequent anti-inflammatory response, and PSC-dependent scarring (Schneider and Whitcomb 2002, *Best Pract Res Clin Gastroenterol* 16:347; Witt et al. 2007, *Gastroenterology* 132:1557; Whitcomb 1999, *Gut* 45:317; Kloppel and Maillet 1993, *Pancreas* 8:659; Comfort et al. 1946, *Gastroenterology* 6:376). Recurrent pancreatic injury overwhelms normal repair mechanisms, favoring progressive irreversible fibrosis (Schneider and Whitcomb 2002, *Best Pract Res Clin Gastroenterol* 16:347; Witt et al. 2007, *Gastroenterology* 132:1557; Whitcomb 1999, *Gut* 45:317). Compounds described herein have been developed to limit repeated pancreatic injury, and thus minimize the progression of CP.

I. Apigenin and Related Compounds

Natural products, especially common dietaries consumed on a daily basis, continue to serve as a valuable source in developing drug-like candidates for chemoprevention and chemotherapy (Koehn and Carter 2005, *Nat Rev Drug Discov* 4:206; Harvey 2008, *Drug Discov Today* 13:894; Li and Vederas 2009, *Science* 325:161). Flavonoids, which are ubiquitously distributed in many dietary plant materials, have received a great deal of attention because some of them have been shown to exert various beneficial effects on human health (Srinivas 2009, *Curr Clin Pharmacol* 4:67).

Apigenin (4',5,7-trihydroxyflavone) is found in many plants, is a natural product belonging to the flavone class that is the aglycone of several naturally occurring glycosides. Apigenin is abundantly present in common fruits and vegetables, and has gained particular interest in recent years as a beneficial and health-promoting agent because of its low intrinsic toxicity (Shukla and Gupta 2010, *Pharm Res* 27:962). Apigenin has been demonstrated to possess various clinically relevant properties such as anti-inflammatory, anti-oxidant, antiproliferative, and pro-apoptotic activities likely through multiple mechanisms (Patel et al. 2007, *Int J Oncol* 30:233). Research efforts on this natural product with low intrinsic toxicity have led the inventors to discover that apigenin can ameliorate the stromal fibrosis characteristic of CP.

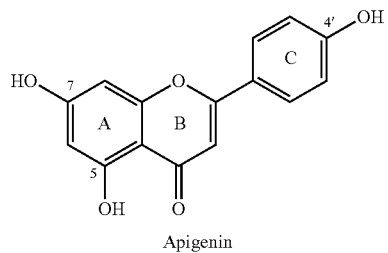

Apigenin

Despite its promising anti-fibrotic property, apigenin suffers from poor aqueous solubility and low metabolic stability like most flavonoids, limiting its clinical potential. While many research groups focused on developing novel compounds based on the apigenin structure as anticancer agents, most of these apigenin derivatives suffered from unfavorable physicochemical properties, including limited aqueous solubility, and none of them has been approved for clinical investigation (Keller et al. 2006, *Curr Opin Chem Biol* 10:357; Di et al. 2009, *Curr Pharm Des* 15:2184). As described herein, the inventors describe the design and synthesis of novel apigenin analogues that suppress the proliferation and promote apoptosis in activated PSC with improved potency and favorable physicochemical properties. The inventors also disclose that at a low dose, analogues 23 and 24 are as efficacious as apigenin in reducing pancreatic fibrosis in a preclinical animal model, providing the proof-of-concept as potential therapeutics for CP.

Considerable efforts on the modifications of apigenin as the lead compound in anticancer drug design have been made. Structure-activity relationship (SAR) studies indicate that the A ring of apigenin as well as its C ring are suitable for modifications (Manthey and Guthrie 2002, *J Agric Food Chem* 50:5837; Chan et al. 2006, *J Med Chem* 49:6742; Lin et al. 2007, *J Med Chem* 50:3921; Wong et al. 2009, *J Med Chem* 52:5311). In addition, studies have demonstrated that the polymethoxylated flavones or flavone analogues with nonpolar and hydrophobic substituents on A ring generally exhibit more potent antiproliferative activities against various human cancer cell lines (Manthey and Guthrie 2002, *J Agric Food Chem* 50:5837; Walle 2007, *Mol Pharm* 4:826). Moreover, methylated flavones have dramatically higher intestinal permeability and higher metabolic stability (Gradolatto et al. 2004, *Drug Metab Dispos* 32:58; Gradolatto et al. 2005, *Drug Metab Dispos* 33:49; Wen and Walle 2006, *Drug Metab Dispos* 34:1786). Combined with the structural features of the SAR trends, optimization efforts were directed to discover novel apigenin derivatives by introducing aqueous solubility-enhancing moieties at 4'-O position of apigenin with 5,7-dimethoxy groups on the A ring.

The synthesis of apigenin derivatives with chemical optimizations on 4'-hydroxyl group is outlined in Scheme 1. The key intermediate 5 was prepared in a three-step synthesis starting with 1-(2-hydroxy-4,6-dimethoxyphenyl)ethanone (2) and 4-allyloxybenzaldehyde (3) according to a literature procedure (Chan et al. 2009, *ChemMedChem* 4:594). As shown in Scheme 1, base-catalyzed aldol condensation of 2 with 3 afforded the chalcone 4 in a yield of 76% with a simple purification. The chalcone was cyclized in the presence of catalytic iodine in dimethyl sulfoxide at 140° C. to provide the flavone 5 in high yield. The allyl protecting group of flavones 5 was cleaved with a catalytic amount of Pd(PPh$_3$)$_4$ in the presence of K$_2$CO$_3$ in MeOH at reflux for 4 hours to obtain the intermediate 4'-hydroxyflavone 6 for direct use without further purification.

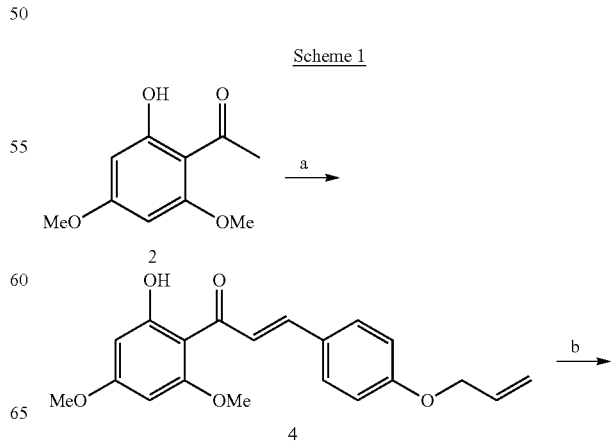

Scheme 1

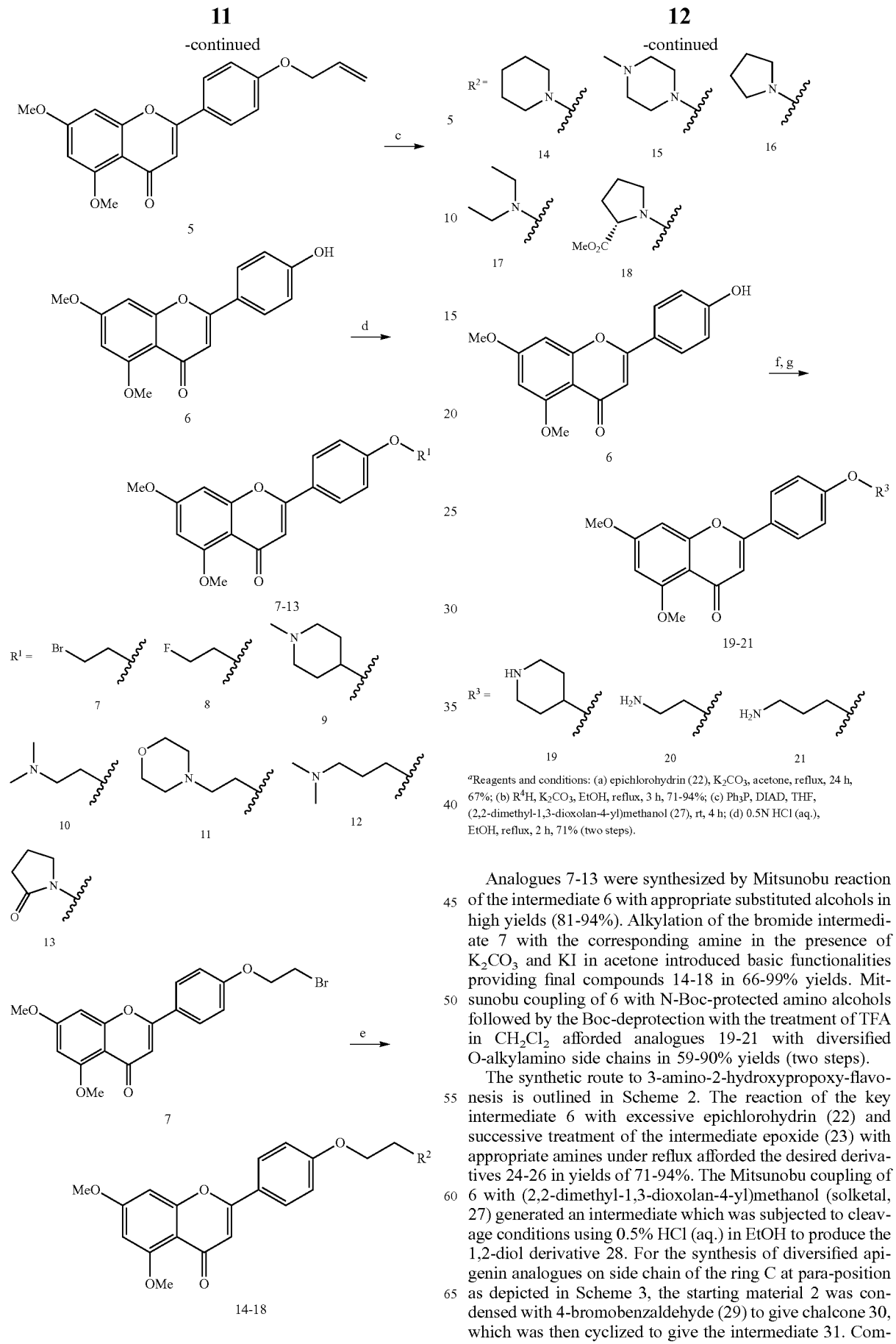

*Reagents and conditions: (a) epichlorohydrin (22), K₂CO₃, acetone, reflux, 24 h, 67%; (b) R⁴H, K₂CO₃, EtOH, reflux, 3 h, 71-94%; (c) Ph₃P, DIAD, THF, (2,2-dimethyl-1,3-dioxolan-4-yl)methanol (27), rt, 4 h; (d) 0.5N HCl (aq.), EtOH, reflux, 2 h, 71% (two steps).

Analogues 7-13 were synthesized by Mitsunobu reaction of the intermediate 6 with appropriate substituted alcohols in high yields (81-94%). Alkylation of the bromide intermediate 7 with the corresponding amine in the presence of K₂CO₃ and KI in acetone introduced basic functionalities providing final compounds 14-18 in 66-99% yields. Mitsunobu coupling of 6 with N-Boc-protected amino alcohols followed by the Boc-deprotection with the treatment of TFA in CH₂Cl₂ afforded analogues 19-21 with diversified O-alkylamino side chains in 59-90% yields (two steps).

The synthetic route to 3-amino-2-hydroxypropoxy-flavonesis is outlined in Scheme 2. The reaction of the key intermediate 6 with excessive epichlorohydrin (22) and successive treatment of the intermediate epoxide (23) with appropriate amines under reflux afforded the desired derivatives 24-26 in yields of 71-94%. The Mitsunobu coupling of 6 with (2,2-dimethyl-1,3-dioxolan-4-yl)methanol (solketal, 27) generated an intermediate which was subjected to cleavage conditions using 0.5% HCl (aq.) in EtOH to produce the 1,2-diol derivative 28. For the synthesis of diversified apigenin analogues on side chain of the ring C at para-position as depicted in Scheme 3, the starting material 2 was condensed with 4-bromobenzaldehyde (29) to give chalcone 30, which was then cyclized to give the intermediate 31. Compound 33 was obtained by Suzuki coupling reaction of 31 with 2-fluoropyridine-5-boronic acid (32) in the presence of Pd(dppf)Cl$_2$ catalyst in a yield of 85%. Palladium-catalyzed Buchwald-Hartwig amination reaction of 31 with N,N-dimethylethylenediamine (34) or 2-(pyrrolidin-1-yl)ethanamine (35) afforded the targeted compounds 36 and 37 in yield of 64% and 57%, respectively.

Scheme 2

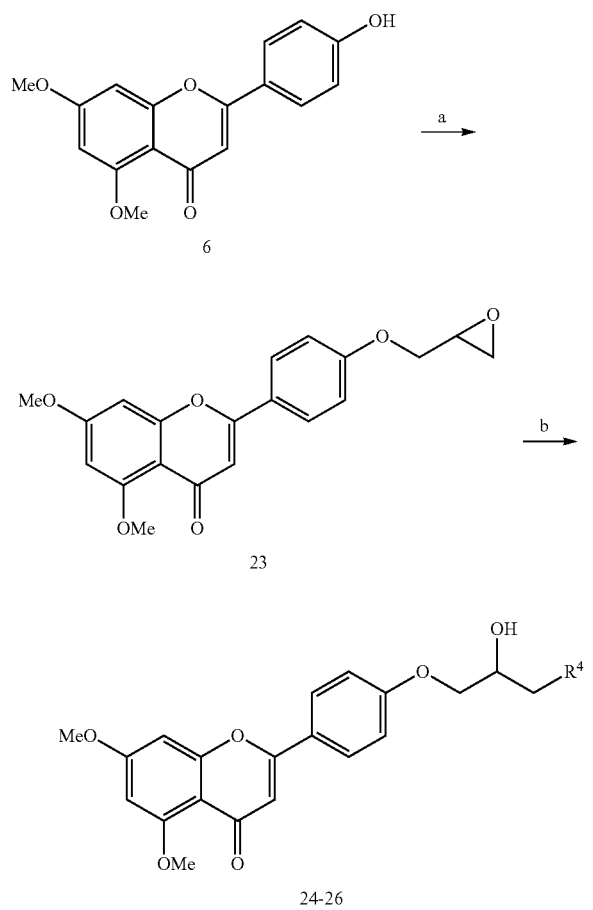

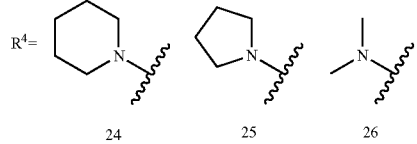

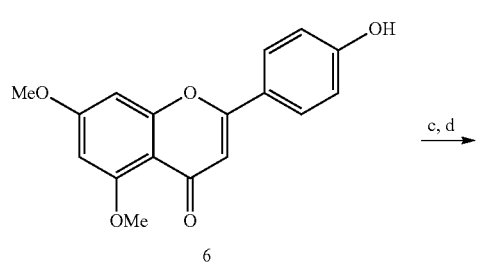

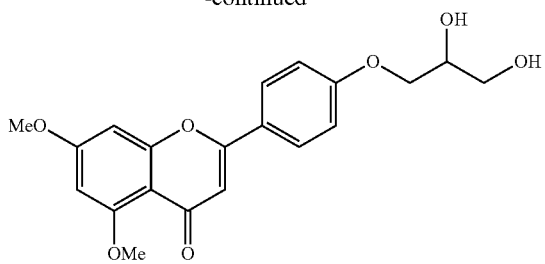

28

$^a$Reagents and conditions: (a) epichlorohydrin (22), K$_2$CO$_3$, acetone, reflux, 24 h, 67%; (b) R$^4$H, K$_2$CO$_3$, EtOH, reflux, 3 h, 71-94%; (c) Ph$_3$P, DIAD, THF, (2,2-dimethyl-1,3-dioxolan-4-yl)methanol (27), rt, 4 h; (d) 0.5N HCl (aq.), EtOH, reflux, 2 h, 71% (two steps).

Scheme 3

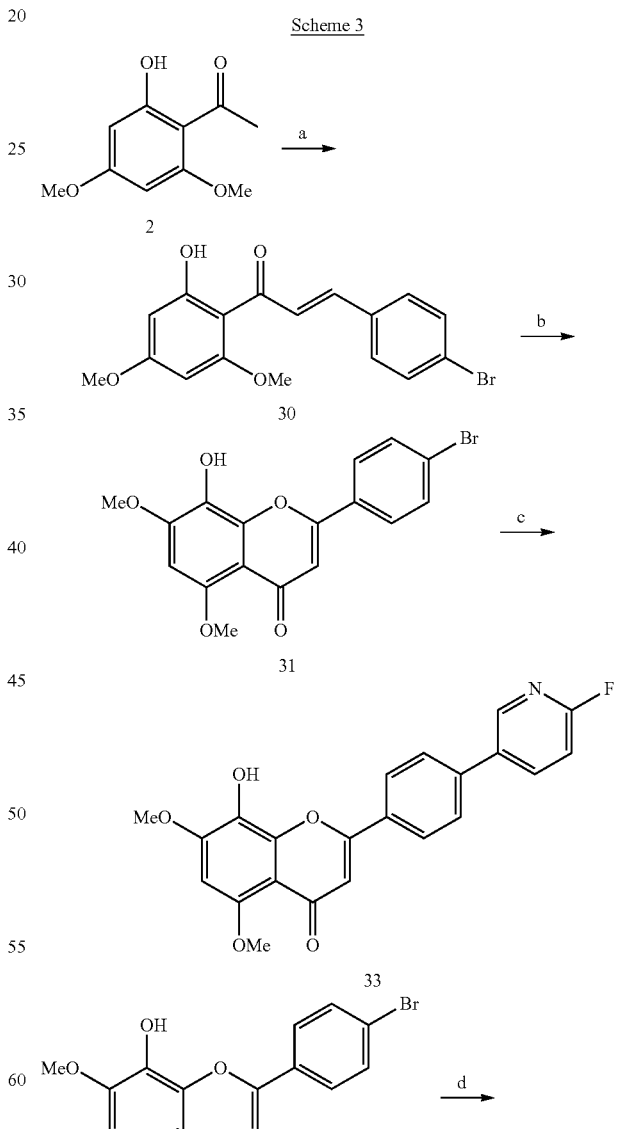

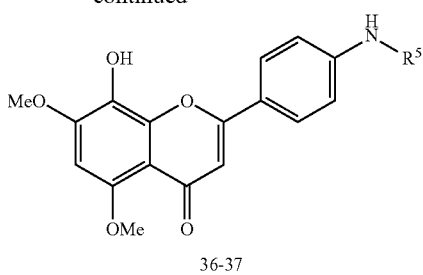

36-37

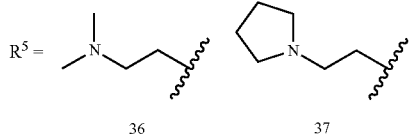

36    37

<sup>a</sup>Reagents and conditions: (a) 4-bromobenzaldehyde (29), 50% NaOH/H$_2$O, EtOH, rt, 16 h, 65%; (b) cat. I$_2$, DMSO, 140° C., 4 h, 92%; (c) 2-fluoropyridine-5-boronic acid (32), Pd(dppf)Cl$_2$, KOAc, THF/EtOH/H$_2$O, 80° C., 18 h, 85%; (d) NH$_2$R$^5$ [N,N-dimethylethylenediamine (34) for 36 or 2-(pyrrolidin-1-yl)ethanamine (35) for 37], Pd$_2$(dba)$_3$, NaO$^t$Bu, (±)-BINAP, toluene, 80° C., 48 h, 57-64%.

Scheme 4 outlines the synthesis of demethylated derivatives 38 and 39. Generation of 38 was achieved in 79% yield by a mono-demethylation of 16 using 2 equiv of boron tribromide at room temperate for 2 h. Both methyl groups on A-ring of 16 were successfully removed by treatment with 3 equiv of boron tribromide for 24 h, leading to the demethylated analogue 39 in a yield of 73%.

Scheme 4

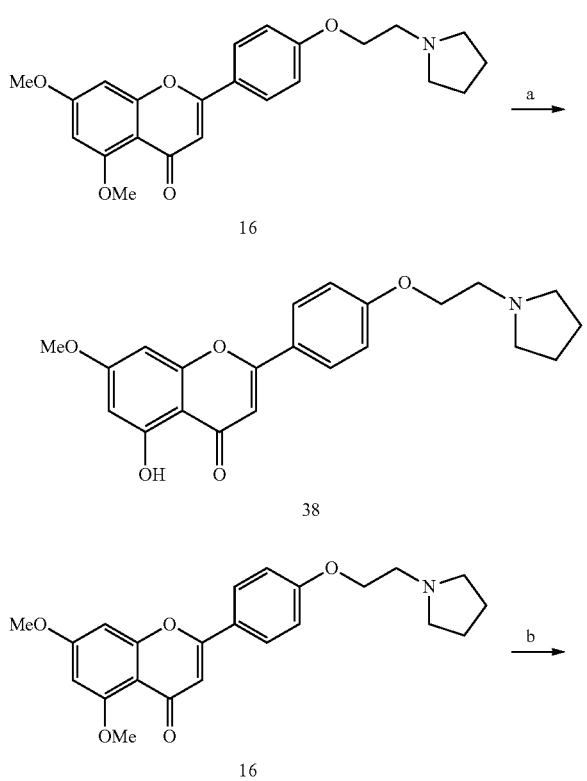

<sup>a</sup>Reagents and conditions: (a) 1N BBr$_3$ (in CH$_2$Cl$_2$), CH$_2$Cl$_2$, rt. 2 h, 79%; (b) 1N BBr$_3$ (in CH$_2$Cl$_2$), CH$_2$Cl$_2$, rt, 24 h, 73%.

The calculated lipophilicity (cLogP) and topological polar surface area (tPSA) values of synthesized analogues are listed in Table 1. The results indicate that these compounds meet the criteria of Lipinski's "Rule of Five" and may have favorable physicochemical properties. To explore a meaningful SAR and examine how the substitutions on the key moieties affect biological activities of apigenin derivatives, the inventors first evaluated the in vitro antiproliferative effects of these analogues on transformed PSC using AlamarBlue Cell Viability Assay (Life Technologies) as described below. AlamarBlue is a non-toxic reagent that is converted to a highly fluorescent end product by viable cells. The capabilities of these new analogues to inhibit the proliferation of transformed PSC are summarized in Table 1.

TABLE 1

Effects of apigenin and newly synthesized apigenin analogues on PSC proliferation.

| Entry | cLogP$^a$ | tPSA$^b$ | Inhibitory Effect (%)$^c$ | | |
|---|---|---|---|---|---|
|  |  |  | 5 μM | 10 μM | 20 μM |
| Apigenin (1) | 2.33 | 90.9 | 11% | 34% | 64% |
| 6 | 2.73 | 68.9 | NE$^d$ | NE | NE |
| 7 | 3.86 | 57.9 | NE | NE | 20% |
| 8 | 3.35 | 57.9 | NE | NE | 21% |
| 9 | 3.29 | 61.2 | 28% | 49% | ND$^e$ |
| 10 | 2.73 | 61.2 | 19% | 51% | 65% |
| 11 | 2.45 | 70.4 | NE | NE | NE |
| 12 | 3.06 | 61.2 | 36% | 59% | 86% |
| 13 | 2.69 | 78.2 | 7% | 14% | 33% |
| 14 | 3.84 | 61.2 | 45% | 64% | 97% |
| 15 | 2.66 | 64.4 | 22% | 42% | 67% |
| 16 | 3.48 | 61.2 | 48% | 66% | 98% |
| 17 | 3.54 | 61.2 | 33% | 60% | 72% |
| 18 | 3.22 | 87.5 | 22% | 37% | 67% |
| 19 | 3.08 | 69.9 | NE | 21% | ND |
| 20 | 1.93 | 83.9 | 6% | 35% | 70% |
| 21 | 2.43 | 83.9 | 22% | 39% | ND |
| 23 | 2.50 | 70.4 | 69% | 89% | 93% |
| 24 | 3.03 | 81.4 | 34% | 65% | 95% |
| 25 | 2.66 | 81.4 | 21% | 37% | 57% |
| 26 | 2.13 | 81.4 | 42% | 60% | 71% |
| 28 | 1.77 | 98.4 | NE | 11% | 16% |
| 31 | 3.80 | 48.7 | 12% | 10% | 22% |
| 33 | 4.05 | 61.6 | NE | 6% | 19% |
| 36 | 2.72 | 63.9 | 30% | 60% | 84% |
| 37 | 3.13 | 63.9 | 21% | 51% | 80% |
| 38 | 3.28 | 72.1 | NE | 39% | 99% |
| 39 | 2.98 | 83.1 | 2% | 71% | 90% |

$^a$cLogP: see URL 146.107.217.178/lab/alogps/start.html.
$^b$tPSA: see worldwideweb at molinspiration.com/cgi-bin/properties.
$^c$Values are mean of at least three independent experiments.
$^d$NE: No effect.
$^e$ND: Not determined.

Intermediate 6 was found to display no significant antiproliferative effect even at 20 μM. After introduction of an O-bromoalkyl moiety or an O-fluoroalkyl moiety into the derivative 6 at 4'-O position, compounds 7 and 8 showed a slightly increased antiproliferative effects in comparison with 6, indicating that appropriate modifications on 4'-O position may regain the antiproliferative activity. O-Alkylamino-tethered derivatives 9, 10 and 12 exhibited a moderate antiproliferative activity at 10 µM with inhibitory effects of 49%, 51%, and 59%, respectively. This finding suggests that optimization with a nitrogen-containing hydrophilic moiety at 4'-O position appears to be a viable strategy to yield more potent compounds with a better aqueous solubility. To this end, compounds 14 with a piperidinyl moiety and 16 with a pyrrolidinyl group displayed potent antiproliferative activity at 10 µM with inhibitory effects of 64% and 66%, respectively.

Meanwhile, it was found that the tertiary amines with alkylated amino groups appeared to be more favorable than secondary or primary amines with free amino groups at the terminal of the side chains. For instance, in comparison with compounds 14 and 16, analogues 19-21 only exhibited a moderate to low inhibitory effects. The similar trend of SAR was also observed for derivatives 24-26 and 28. Compound 28 with a terminal OH group at the tail resulted in a dramatic loss of activities compared with analogues 24-26 with a terminal amino moiety. Interestingly, compound 23 with an epoxide was identified as a highly potent inhibitor suppressing PSC proliferation.

Structural modifications of para-position on C-ring with diversified substitutions were also investigated. Compound 33 with a pyridinyl group on the para-position resulted in a substantial loss of the activity. In contrast, introduction of 2-dimethylamino-ethylamino moiety or 2-pyrrolidin-1-yl-ethylamino group displayed significantly better antiproliferative activities at 10 µM with inhibitory effects of 60% and 51%, respectively. Demethylation of compound 16 resulted in generation of two O-demethylated compounds 38 and 39. It was found that neither mono-demethylation nor full demethylation of the methoxy groups on the A-ring is favorable for the enhancement of activity, and thus more extensive SAR study on the A-ring was not pursued.

Since one goal of the drug discovery effort was to identify new apigenin derivatives with improved water-solubility and oral bioavailability, aqueous solubility of several selected analogues with enhanced antiproliferative effects was determined by an HPLC analysis method (Chen et al. 2013, *ACS Med Chem Lett* 4:180). As depicted in FIG. 1, compounds 14, 16 and 24 (in the form of HCl salt) have demonstrated to possess more favorable aqueous solubility, with a saturated concentration of 17.4, 13.7 and 84.1 mg/mL, respectively, while that of apigenin is only 2.16 µg/mL (Keller et al. 2006, *Curr Opin Chem Biol* 10:357).

Figure 2:
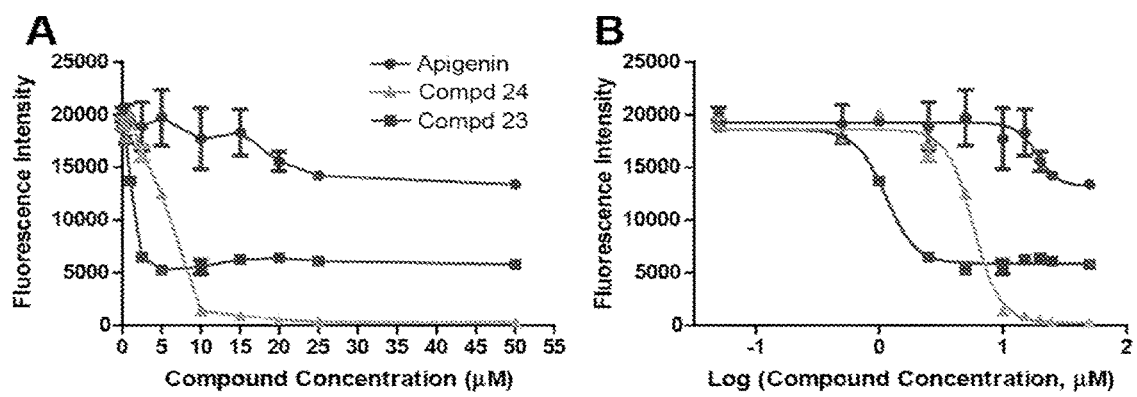
FIG. 2. Effect of apigenin and its analogues on PSC proliferation. Human PSC were treated with apigenin or analogues at various doses for 24 h. (A) Representative data from one experiment: cell viability was measured using the AlamarBlue colorimetric assay. (B) The $IC_{50}$ values of apigenin, 23, and 24 are 18.6±1.6 µM, 2.5±0.6 µM, and 8.0±1.8 µM, respectively. The calculated $IC_{50}$ values are derived from the mean±SEM of at least three independent experiments.

To investigate more detailed information about the antiproliferative effects of this series of apigenin derivatives against human PSC, compounds 23 (HJC0561) and 24 (HJC05100) were selected based on their potency or aqueous solubility for further evaluations using cell proliferation and cell death assays, as well as an in vivo model of CP. As shown in FIG. 2A, both analogues 23 and 24 inhibited PSC proliferation at lower doses than apigenin, indicating enhanced potency in vitro. With logarithmic transformation and nonlinear regression, a best-fit curve was generated, allowing determination of their $IC_{50}$, representing the concentration at which the compound causes 50% inhibition of PSC proliferation (FIG. 2B). Compound 23 was identified as a highly potent analogue with an $IC_{50}$ value of 2.5±0.6 µM. Compound 24 was slightly less potent with an $IC_{50}$ value of 8.0±1.8 µM, and that of apigenin was 18.6±1.6 µM. The irreversible fibrosis that defines CP is mediated by activated PSC, which produce and remodel the extracellular matrix (ECM) (Erkan et al. 2012, *Gut* 61:172). Therefore, the potent antiproliferative effect of these new analogues on PSC supports their further development as anti-fibrotic agents for CP.

Figure 3:
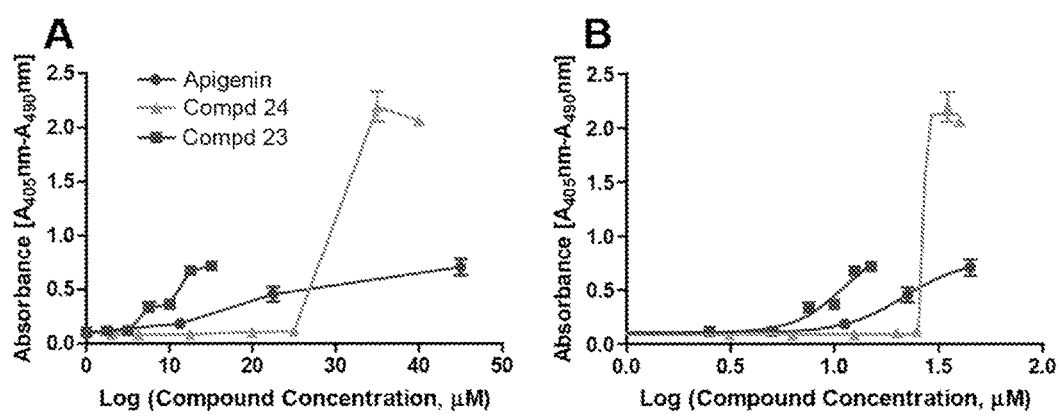
FIG. 3. Effect of apigenin and its analogues on PSC apoptosis. Human PSC were treated with apigenin or analogues at various doses for 14 h. (A) Representative data from one experiment: Apoptosis was measured using the Cell Death Detection ELISA$^{PLUS}$ assay. (B) The $EC_{50}$ values of apigenin, 23, and 24 are 24.5±2.5 µM, 9.6±1.8 µM, and 35.2±5.5 µM, respectively. The calculated $EC_{50}$ values are derived from the mean±SEM of at least three independent experiments.

These two representative analogues were also investigated to determine whether the growth inhibition induced by compounds 23 and 24 in PSC was attributed to apoptosis. Apoptosis was determined using the Cell Death Detection ELISA$^{PLUS}$ assay. This sandwich-enzyme-immunoassay involved antibodies binding to cytoplasmic nucleosomes, which were specific to the process of apoptosis rather than necrosis. Analogue 23 was found to be quite potent, inducing greater PSC cell death at lower concentrations than apigenin (FIG. 3A). At low concentrations, compound 24 failed to induce apoptosis; however, between the concentrations of 25-35 µM, it produced a steep dose-response curve, and concentrations beyond 35 µM induced significant cell death. Next, the dose-response curve was generated (FIG. 3B). The $EC_{50}$ represented the concentration at which the compound yielded half of the maximal amount of cell death. The most potent analogue 23 exhibited the lowest $EC_{50}$ value of 9.6±1.8 µM, while the $EC_{50}$ value of apigenin was 24.5±2.5 µM, and that of 24 was 35.2±5.5 µM. The capacity of the compounds to induce cell death in activated PSC would most likely translate into reduced fibrosis in CP. Analogue 23 more potently induced PSC apoptosis than apigenin, while 24 appeared to act through a different cellular mechanism, inducing stellate cell toxicity at concentrations greater than 25 µM.

Figure 4:
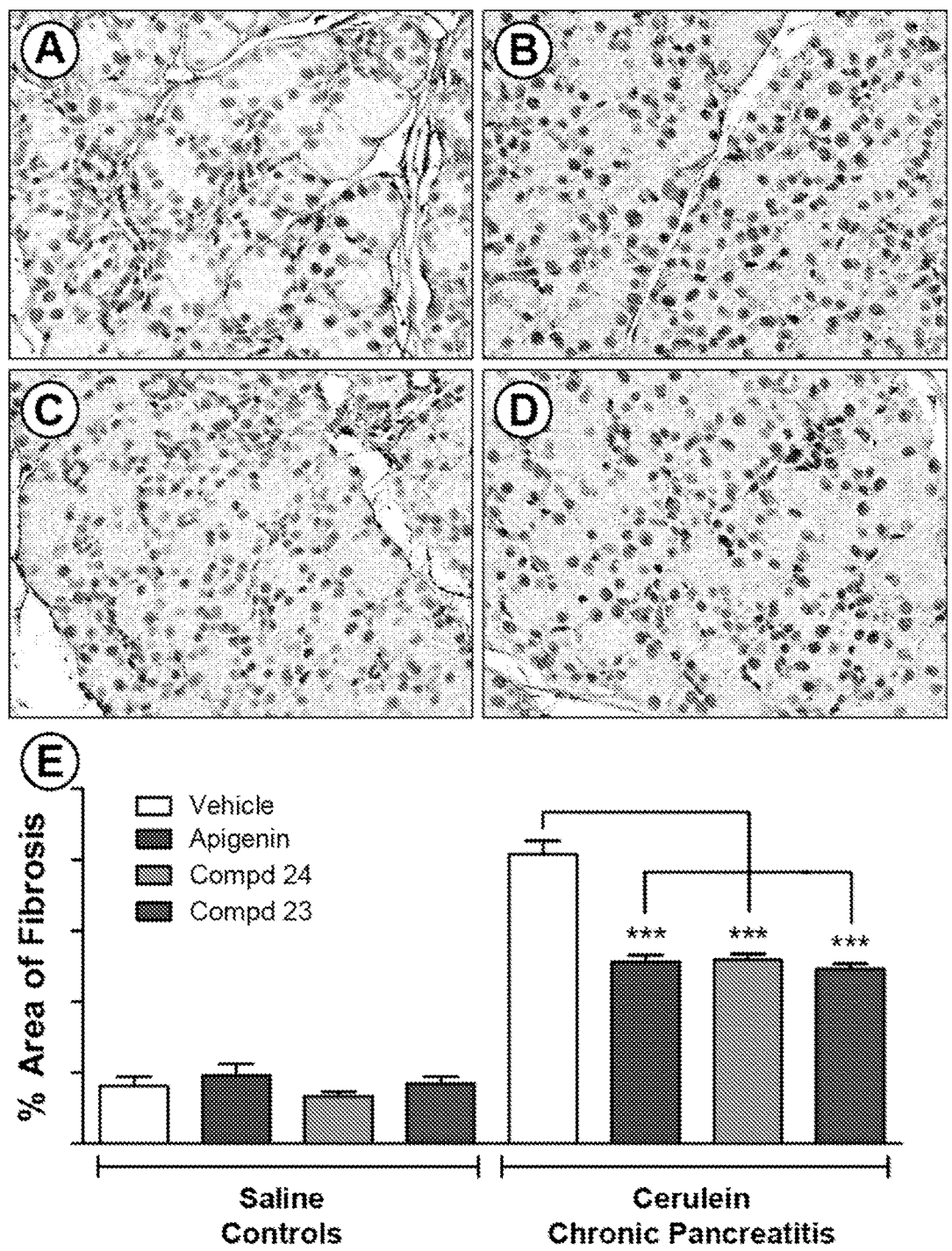
FIG. 4. Effect of apigenin and its analogues in preclinical animal model of CP. CP was induced using repeated cerulean (CR) injections as outlined in the methods. Control mice received PBS (n=5), and mice injected with CR developed CP (n=10-11). Treatment with vehicle (0.5% methylcellulose+0.025% Tween 20 in dd$H_2O$), apigenin or analogues (0.5 mg/kg, daily gavage) started the second week and was continued 3 additional weeks while continuing CP induction. Pancreata were stained for fibronectin by IHC, and counter-stained with hematoxylin. Representative 400× images of each group are shown: (A) CR+Vehicle; (B) CR+Apigenin; (C) CR+24; and (D) CR+23. ImageJ analysis of the slides quantified the percent area of brown fibronectin stain in (E). * * * represents p<0.001, comparing to the effect from apigenin at the same dosage.

These results prompted the further testing of 23 and 24 as lead compounds for the development of a new series of anti-fibrotic agents that may be useful for treating CP (Apte 2011, *Antioxid Redox Signal* 15:2711). In order to evaluate the anti-fibrotic effect of these new compounds as a proof-of-concept, the compounds were tested in a preclinical animal model of CP. CP was induced in mice using the well-established model of repeated cerulean (CR) injections (Lerch and Gorelick 2013, *Gastroenterology* 144:1180; Aghdassi et al. 2011, *Fibrogenesis Tissue Repair* 4:26). Treatment with vehicle, apigenin or analogues (0.5 mg/kg daily gavage) was started the second week of the experiment and continued with CP induction. After four weeks, the pancreata were processed and stained for fibronectin, which is a major component of the ECM. The 400×microscope image in FIG. 4A showed a large amount of periacinar and perilobular fibrosis (brown color), edema (the space between lobules), and atrophic, irregularly shaped acini (Chao et al. 2005, *J Surg Res* 129:313). Treatment with apigenin and analogues 23 and 24 significantly decreased the stromal fibrosis of CP, reduced tissue edema, and limited acinar cell damage (FIGS. 4B-4D). ImageJ analysis of the slides quantified the significant decrease in fibrosis (p<0.001) (FIG. 4E). Despite no statistical difference between apigenin and compounds 23 or 24 at the low dose of 0.5 mg/kg, these data demonstrated that apigenin and new analogues significantly reduced fibrosis in the pre-clinical animal model of CP. Proof-of-concept studies are provided herein and demonstrate that apigenin and analogues have the potential to function as anti-fibrotic agents in CP.

Accumulating evidence suggests that activated PSC play an important role in CP. The inventors have contemplated a strategy for the prevention and treatment of CP by decreasing the proliferation and inducing apoptosis of PSC. While a few flavone-based compounds have previously been reported to possess antiproliferative effects for cancer, the inventors show that apigenin and its analogues suppress the proliferation of PSC and reduce the associated fibrosis. Chemical modifications of apigenin have been directed to build a focused library of O-alkylamino-tethered apigenin derivatives at 4'-O position of the ring C with the attempt to enhance the potency and drug-like properties including aqueous solubility. A series of novel apigenin analogues have been synthesized from the key intermediate 6, and a number of compounds such as 14, 16, and 24 have been identified to exhibit potent antiproliferative effects as well as improved aqueous solubility. Even at a low dose of 0.5 mg/kg apigenin, new analogues 23 and 24 significantly reduced the fibrotic response in a preclinical animal model of CP, providing a proof-of-concept study that supports their development as promising therapeutics for CP.

II. Chemical Definitions

Various chemical definitions related to such compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" means that the compound dissolves in water at least to the extent of 0.010 mole/liter or is classified as soluble according to literature precedence.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

As used herein, the term "nitro" means $-NO_2$; the term "halo" designates $-F$, $-Cl$, $-Br$ or $-I$; the term "mercapto" means $-SH$; the term "sulfonate ester" means $-OSO_2R'$, the term "cyano" means $-CN$; the term "azido" means $-N_3$; the term "imino" means $=NH$; the term "azo" means $-RN=NR$; the term "thioyl" means $-SH$; the term "sulfonyl" means $-SO_2R$; The term "sulfinyl" means $-S(O)R$; the "sulfo" means $-SO_3$; the term "silyl" means $-SiH_3$, the term "hydroxy" means $-OH$, and the term "hydroxyalkyl" means $-ROH$.

The term "amino" means a group having the structure $-NR'R''$ (the term includes primary, secondary, and tertiary amines), the term "amide" means $-C(O)NR'R''$. R' and R'' are independently hydrogen or an optionally substituted alkyl, heteroalkyl, cycloalkyl, or heterocyclyl group.

The term "oxo" as used herein means an oxygen that is double bonded to a carbon atom.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, $-CH_3$ (Me), $-CH_2CH_3$ (Et), $-CH_2CH_2CH_3$ (n-Pr), $-CH(CH_3)_2$ (iso-Pr), $-CH_2CH_2CH_2CH_3$ (n-Bu), $-CH(CH_3)CH_2CH_3$ (sec-butyl), $-CH_2CH(CH_3)_2$ (iso-butyl), $-C(CH_3)_3$ (tert-butyl), $-CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, $-CH_2F$, $-CH_2Cl$, $-CH_2Br$, $-CH_2OH$, $-CH_2OCH_3$, $-CH_2OCH_2CF_3$, $-CH_2OC(O)CH_3$, $-CH_2NH_2$, $-CH_2NHCH_3$, $-CH_2N(CH_3)_2$, $-CH_2CH_2Cl$, $-CH_2CH_2OH$, $CH_2CH_2OC(O)CH_3$, $-CH_2CH_2NHCO_2C(CH_3)_3$, and $-CH_2Si(CH_3)_3$.

The terms "alkenyl" and "alkynyl" refer to unsaturated aliphatic groups analogous in length and possible substitution to the alkyls described above, but that contain at least one double or triple bond respectively. Alkenyl or alkynyl are optionally substituted.

The term "alkylsulfonyl" as used herein means a moiety having the formula $-S(O_2)-R'$, where R' is an alkyl group. R' may have a specified number of carbons (e.g. "$C_{1-4}$ alkylsulfonyl"). Alkylsulfonyl is optionally substituted.

The term "alkoxy" means a group having the structure $OR'$, where R' is an optionally substituted alkyl or cycloalkyl group. The term "heteroalkoxy" similarly means a group having the structure $-OR$, where R is a heteroalkyl or heterocyclyl. Alkoxy is optionally substituted.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Cycloalkyl or heterocyclyl can be saturated or unsaturated or polyunsaturated. Heterocycle include, but are not limited to aziridine, azirine, oxirane (ethylene oxide, epoxides), oxirene, thiirane (episulfides), thiirene, diazirine, oxaziridine, dioxirane, azetidine, azete, oxetane, oxete, thietane, thiete, diazetidine, dioxetane, dioxete, dithietane, dithiete, pyrrolidine, pyrrole, tetrahydrofuran, furan, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, triazoles, furazan, oxadiazole, thiadiazole, dithiazole, piperidine, pyridine, oxane, pyran, thiane, thiopyran, piperazine, diazines, morpholine, oxazine, thiomorpholine, thiazine, dioxane, dioxine, dithiane, dithiine, and the like.

The term "aryl" means a polyunsaturated hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl (—C(O)NR$_2$), unsubstituted alkyl, unsubstituted heteroalkyl, alkoxy, alkylthio, alkylamino, (alkyl)$_2$amino, alkylsulfinyl, alkylsulfonyl, arylsulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), —SO$_2$(C$_{1-4}$alkyl), —CO$_2$(C$_{1-4}$alkyl), and —O(C$_{1-4}$alkyl).

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All commercially available starting materials and solvents were reagent grade, and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). Visualization of the developed chromatograms was performed with detection by UV (254 nm). NMR spectra were recorded on a Bruker-600 ($^1$H, 600 MHz; $^{13}$C, 150 MHz) spectrometer. $^1$H and $^{13}$C NMR spectra were recorded with TMS as an internal reference. Chemical shifts were expressed in ppm, and J values were given in Hz. High-resolution mass spectra (HRMS) were obtained from Thermo Fisher LTQ Orbitrap Elite mass spectrometer. Parameters include the following: Nano ESI spray voltage was 1.8 kV; Capillary temperature was 275° C. and the resolution was 60,000; Ionization was achieved by positive mode. Melting points were measured on a Thermo Scientific Electrothermal Digital Melting Point Apparatus and uncorrected. Purity of final compounds was determined by analytical HPLC, which was carried out on a Shimadzu HPLC system (model: CBM-20A LC-20AD SPD-20A UV/VIS). HPLC analysis conditions: Waters µBondapak C18 (300× 3.9 mm); flow rate 0.5 mL/min; UV detection at 270 and 254 nm; linear gradient from 30% acetonitrile in water [0.1%, trifluoroacetic acid (TFA)] to 100% acetonitrile (0.1% TFA) in 20 min followed by 30 min of the last-named solvent. All biologically evaluated compounds are >95% pure.

EXAMPLE 1

2-(4-Hydroxy-phenyl)-5,7-dimethoxy-chromen-4-one (6)

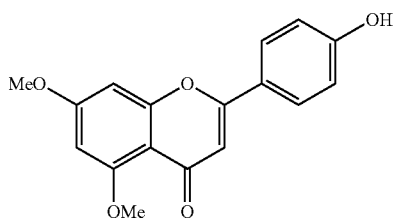 [SMILES: COc1cc(OC)c2c(=O)cc(-c3ccc(O)cc3)oc2c1]

Starting from the commercially available 4-allyloxybenzaldehyde (3) and 1-(2-hydroxy-4,6-dimethoxy-phenyl)-ethanone (2), the key intermediate 6 was prepared in three steps according to literature procedures (Chan et al. 2009, *ChemMedChem* 4:594). HPLC purity 97.0% ($t_R$=16.94 min). $^1$H NMR (600 MHz, DMSO-$d_6$) δ 7.88 (d, 2H, J=9.0 Hz), 6.90 (d, 2H, J=9.0 Hz), 6.83 (d, 1H, J=2.4 Hz), 6.58 (s, 1H), 6.49 (d, 1H, J=2.4 Hz), 3.89 (s, 3H), 3.82 (s, 3H). HRMS (ESI) calcd for $C_{17}H_{15}O_5$ 299.0914 (M+H)$^+$, found 299.0917.

EXAMPLE 2

2-(4-(2-Bromoethoxy)phenyl)-5,7-dimethoxy-chromen-4-one (7, HJC-5-14)

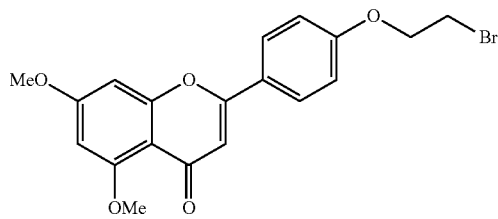 [SMILES: COc1cc(OC)c2c(=O)cc(-c3ccc(OCCBr)cc3)oc2c1]

To a solution of 6 (200 mg, 0.67 mmol) and Ph$_3$P (351 mg, 1.34 mmol) in THF (10 mL) was added 2-bromoethanol (168 mg, 1.34 mmol) and diisopropylazodicarboxylate (DIAD, 271 mg, 1.34 mmol). The mixture was stirred at r.t. for 16 h. The reaction mixture was diluted with ethyl acetate (EtOAc, 200 mL) and extracted with H$_2$O (40 mL). The organic layer was washed with brine (10 mL), dried over anhydrous Na$_2$SO$_4$, and concentrated to give the crude product. This residue was purified with silica gel column (EtOAc) to provide 7 (240 mg, 88%) as a white solid (mp 202-203° C.). HPLC purity 99.6% ($t_R$=21.17 min). $^1$H NMR (600 MHz, DMSO-$d_6$) δ 8.00 (d, 2H, J=8.4 Hz), 7.12 (d, 2H, J=9.0 Hz), 6.86 (d, 1H, J=2.4 Hz), 6.68 (s, 1H), 6.50 (d, 1H, J=1.8 Hz), 4.43 (t, 2H, J=5.4 Hz), 3.90 (s, 3H), 3.85 (t, 2H, J=5.4 Hz), 3.83 (s, 3H). $^{13}$C NMR (150 MHz, DMSO-$d_6$) δ 175.6, 163.6, 160.4, 160.2, 159.5, 159.1, 127.8, 123.5, 115.1, 108.3, 106.9, 96.2, 93.4, 68.0, 56.1, 56.0, 31.2. HRMS (ESI) calcd for $C_{19}H_{18}BrO_5$ 405.0332 (M+H)$^+$, found 405.0334.

EXAMPLE 3

2-(4-(2-Fluoroethoxy)phenyl)-5,7-dimethoxy-chromen-4-one (8, HJC-5-54)

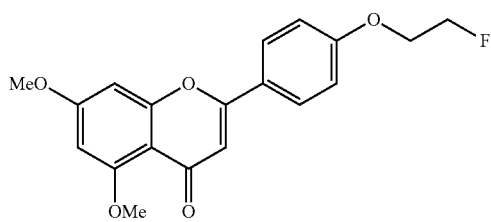 [SMILES: COc1cc(OC)c2c(=O)cc(-c3ccc(OCCF)cc3)oc2c1]

Compound 8 was prepared in 90% yield by a procedure similar to that used to prepare 7. The title compound was obtained as a white solid (mp 187-188° C.). HPLC purity 97.3% ($t_R$=19.56 min). $^1$H NMR (600 MHz, CDCl$_3$) δ 7.82 (d, 2H, J=10.2 Hz), 7.03 (d, 2H, J=10.2 Hz), 6.59 (s, 1H), 6.55 (d, 1H, J=2.4 Hz), 6.37 (d, 1H, J=1.8 Hz), 4.82-4.84 (m, 1H), 4.74-4.76 (m, 1H), 4.30-4.32 (m, 1H), 4.26-4.27 (m, 1H), 3.95 (s, 3H), 3.91 (s, 3H). $^{13}$C NMR (150 MHz, CDCl$_3$) δ 177.8, 164.1, 161.0, 160.9, 160.6, 160.0, 127.8, 124.6, 115.1, 109.4, 108.0, 96.2, 93.0, 81.9 (d, J=171.5 Hz), 67.4 (d, J=20.3 Hz), 56.6, 55.9. HRMS (ESI) calcd for $C_{19}H_{18}FO_5$ 345.1133 (M+H)$^+$, found 345.1135.

EXAMPLE 4

5,7-Dimethoxy-2-(4-(1-methylpiperidin-4-yloxy)phenyl)-chromen-4-one (9, HJC-5-38)

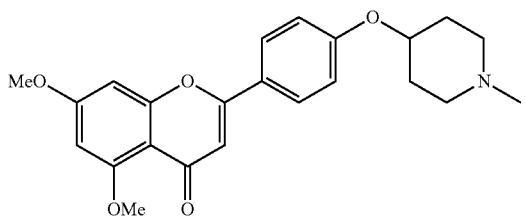 [SMILES: COc1cc(OC)c2c(=O)cc(-c3ccc(OC4CCN(C)CC4)cc3)oc2c1]

Compound 9 was prepared in 94% yield by a procedure similar to that used to prepare 7. The title compound was obtained as a white solid (mp 143-144° C.). HPLC purity 99.3% ($t_R$=15.86 min). $^1$H NMR (600 MHz, CDCl$_3$) δ 7.80 (d, 2H, J=9.0 Hz), 6.99 (d, 2H, J=9.0 Hz), 6.58 (s, 1H), 6.55 (d, 1H, J=2.4 Hz), 6.37 (d, 1H, J=3.0 Hz), 4.44 (s, 1H), 3.95 (s, 3H), 3.91 (s, 3H), 2.72 (s, 2H), 2.38 (s, 2H), 2.34 (s, 3H), 2.04-2.08 (m, 2H), 1.88-1.92 (m, 2H). $^{13}$C NMR (150 MHz, CDCl$_3$) δ 177.8, 164.0, 161.0, 160.8, 160.1, 160.0, 127.8, 123.9, 116.2, 109.4, 107.8, 96.2, 93.0, 56.6, 55.9, 52.4, 46.1, 30.6. HRMS (ESI) calcd for $C_{23}H_{26}NO_5$ 396.1806 (M+H)$^+$, found 396.1808.

EXAMPLE 5

2-(4-(2-Dimethylaminoethoxy)phenyl)-5,7-dimethoxy-chromen-4-one (10, HJC-5-15)

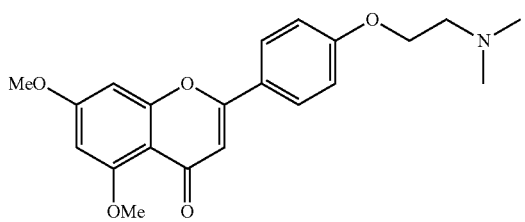 [SMILES: COc1cc(OC)c2c(=O)cc(-c3ccc(OCCN(C)C)cc3)oc2c1]

Compound 10 was prepared in 81% yield by a procedure similar to that used to prepare 7. The title compound was obtained as a pale yellow solid (mp 153-154° C.). HPLC purity 98.8% ($t_R$=15.25 min). $^1$H NMR (600 MHz, CDCl$_3$) δ 7.81 (d, 2H, J=9.0 Hz), 7.02 (d, 2H, J=9.0 Hz), 6.59 (s, 1H), 6.55 (d, 1H, J=1.8 Hz), 6.37 (d, 1H, J=1.8 Hz), 4.14 (t, 2H, J=6.0 Hz), 3.95 (s, 3H), 3.91 (s, 3H), 2.78 (t, 2H, J=6.0 Hz), 2.36 (s, 6H). $^{13}$C NMR (150 MHz, CDCl$_3$) δ 177.8, 164.0, 161.4, 161.0, 160.8, 160.0, 127.7, 124.1, 115.1, 109.4, 107.9, 96.2, 92.9, 66.3, 58.2, 56.6, 55.9, 46.0. HRMS (ESI) calcd for C$_{21}$H$_{24}$NO$_5$ 370.1649 (M+H)$^+$, found 370.1652.

EXAMPLE 6

5,7-Dimethoxy-2-(4-(2-morpholin-4-yl-ethoxy)phenyl)-chromen-4-one (11, HJC-5-16)

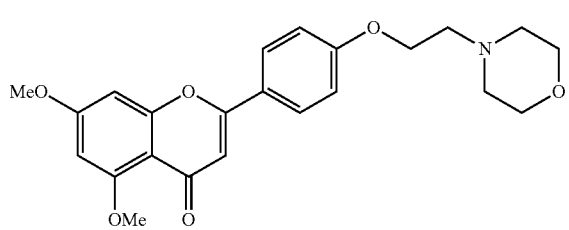 [SMILES: COc1cc(OC)c2c(=O)cc(-c3ccc(OCCN4CCOCC4)cc3)oc2c1]

Compound 11 was prepared in 82% yield by a procedure similar to that used to prepare 7. The title compound was obtained as a white solid (mp 149-150° C.). HPLC purity 99.8% ($t_R$=15.26 min). $^1$H NMR (600 MHz, CDCl$_3$) δ 7.80 (d, 2H, J=9.0 Hz), 6.99 (d, 2H, J=9.0 Hz), 6.58 (s, 1H), 6.55 (s, 1H), 6.37 (s, 1H), 4.18 (t, 2H, J=6.0 Hz), 3.95 (s, 3H), 3.90 (s, 3H), 3.74 (t, 4H, J=3.0 Hz), 2.83 (t, 2H, J=6.0 Hz), 2.59 (s, 4H). $^{13}$C NMR (150 MHz, CDCl$_3$) δ 177.8, 164.1, 161.3, 161.0, 160.7, 160.0, 127.7, 124.2, 115.1, 109.4, 107.9, 96.2, 93.0, 67.0, 66.2, 57.6, 56.6, 55.9, 54.3. HRMS (ESI) calcd for C$_{23}$H$_{26}$NO$_6$ 412.1755 (M+H)$^+$, found 412.1757.

EXAMPLE 7

2-(4-(3-Dimethylaminopropoxy)phenyl)-5,7-dimethoxy-chromen-4-one (12, HJC-5-74)

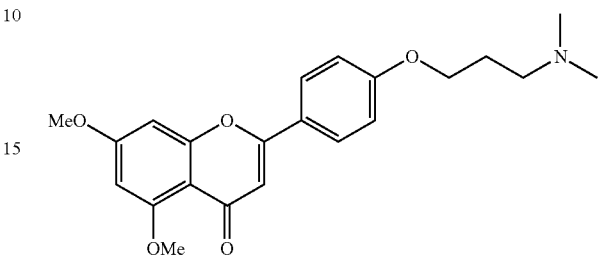

Compound 12 was prepared in 91% yield by a procedure similar to that used to prepare 7. The title compound was obtained as a white solid (mp 105-106° C.). HPLC purity 98.2% ($t_R$=15.76 min). $^1$H NMR (600 MHz, CDCl$_3$) δ 7.81 (d, 2H, J=9.0 Hz), 6.99 (d, 2H, J=9.0 Hz), 6.59 (s, 1H), 6.56 (d, 1H, J=2.4 Hz), 6.37 (d, 1H, J=2.4 Hz), 4.09 (t, 2H, J=9.0 Hz), 3.95 (s, 3H), 3.91 (s, 3H), 2.48 (t, 2H, J=7.2 Hz), 2.27 (s, 6H), 1.98-2.00 (m, 2H). $^{13}$C NMR (150 MHz, CDCl$_3$) δ 177.8, 164.0, 161.7, 161.1, 160.9, 160.0, 127.7, 123.9, 115.0, 109.4, 108.0, 96.2, 93.0, 66.6, 56.6, 56.4, 55.9, 45.6, 27.6. HRMS (ESI) calcd for C$_{22}$H$_{26}$NO$_5$ 384.1806 (M+H)$^+$, found 384.1808.

EXAMPLE 8

1-(2-(4-(5,7-Dimethoxy-4-oxo-4H-chromen-2-yl)phenoxy)ethyl)-pyrrolidin-2-one (13, HJC-5-76)

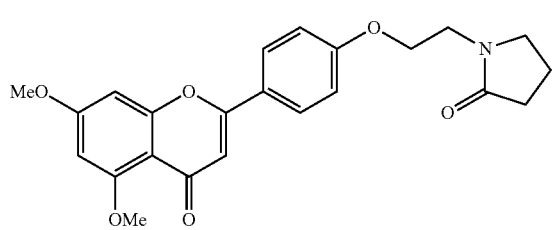 [SMILES: COc1cc(OC)c2c(=O)cc(-c3ccc(OCCN4CCCC4=O)cc3)oc2c1]

Compound 13 was prepared in 85% yield by a procedure similar to that used to prepare 7. The title compound was obtained as a white solid (mp 115-116° C.). HPLC purity 99.3% ($t_R$=18.44 min). $^1$H NMR (600 MHz, CDCl$_3$) δ 7.81 (d, 2H, J=8.4 Hz), 6.97 (d, 2H, J=8.4 Hz), 6.58 (s, 1H), 6.55 (d, 1H, J=2.4 Hz), 6.37 (d, 1H, J=1.8 Hz), 4.18 (t, 2H, J=5.4 Hz), 3.95 (s, 3H), 3.91 (s, 3H), 3.71 (t, 2H, J=5.4 Hz), 3.58 (t, 2H, J=7.2 Hz), 2.39 (t, 2H, J=8.4 Hz), 2.01-2.08 (m, 2H). $^{13}$C NMR (150 MHz, CDCl$_3$) δ 177.8, 175.6, 164.1, 161.0, 160.9, 160.7, 160.0, 127.8, 124.4, 114.9, 109.3, 107.9, 96.2, 92.9, 66.8, 56.6, 55.9, 49.1, 42.4, 30.9, 18.3. HRMS (ESI) calcd for C$_{23}$H$_{24}$NO$_6$ 410.1598 (M+H)$^+$, found 410.1601.

EXAMPLE 9

5,7-Dimethoxy-2-(4-(2-piperidin-1-yl-ethoxy)phenyl)-chromen-4-one (14, HJC-5-56)

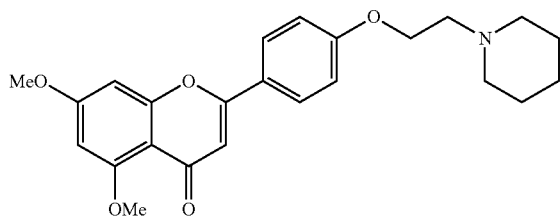 [SMILES: COc1cc(OC)c2c(=O)cc(-c3ccc(OCCN4CCCCC4)cc3)oc2c1]

To a solution of 7 (30 mg, 0.074 mmol), KI (25 mg, 0.15 mmol) and $K_2CO_3$ (102 mg, 0.74 mmol) in acetone (5 mL) was added piperidine (31 mg, 0.37 mmol) at 0° C. The mixture was stirred at 75° C. for 18 h. The solution was diluted with EtOAc (100 mL), washed with 0.1 N HCl (aq.) (10 mL) and brine (10 mL). The organic layer was dried over anhydrous $Na_2SO_4$, and then concentrated under reduced pressure. The residue was purified by silica gel column chromatography (EtOAc) to give the desired product 14 (30 mg, 99%) as a white solid (mp 79-80° C.). HPLC purity 95.1% ($t_R$=16.24 min). $^1$H NMR (600 MHz, CDCl$_3$) δ 7.83 (d, 2H, J=6.6 Hz), 7.02 (d, 2H, J=6.6 Hz), 6.62 (s, 1H), 6.58 (d, 1H, J=2.4 Hz), 6.39 (d, 1H, J=2.4 Hz), 4.22 (t, 2H, J=6.0 Hz), 3.98 (s, 3H), 3.94 (s, 3H), 2.85 (t, 2H, J=6.0 Hz), 2.57-2.59 (m, 4H), 1.65-1.67 (m, 4H), 1.50-1.52 (m, 2H). $^{13}$C NMR (150 MHz, CDCl$_3$) δ 177.8, 164.1, 161.4, 161.0, 160.8, 160.0, 127.7, 124.0, 115.1, 109.4, 107.8, 96.2, 93.0, 66.3, 57.8, 56.6, 55.9, 55.2, 25.9, 24.2. HRMS (ESI) calcd for $C_{24}H_{28}NO_5$ 410.1962 (M+H)$^+$, found 410.1964.

EXAMPLE 10

5,7-Dimethoxy-2-(4-(2-(4-methylpiperazin-1-yl)ethoxy)phenyl)-chromen-4-one (15, HJC-5-53)

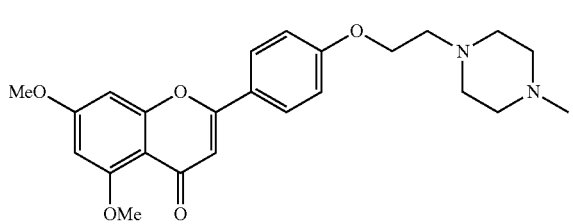 [SMILES: COc1cc(OC)c2c(=O)cc(-c3ccc(OCCN4CCN(C)CC4)cc3)oc2c1]

Compound 15 was prepared in 80% yield by a procedure similar to that used to prepare 14. The title compound was obtained as a white solid (mp 144-145° C.). HPLC purity 98.7% ($t_R$=16.43 min). $^1$H NMR (600 MHz, CDCl$_3$) δ 7.79-7.81 (m, 2H), 6.98-7.00 (m, 2H), 6.58 (s, 1H), 6.55 (d, 1H, J=2.4 Hz), 6.36 (d, 1H, J=2.4 Hz), 4.17 (t, 2H, J=6.0 Hz), 3.95 (s, 3H), 3.90 (s, 3H), 2.85 (t, 2H, J=6.0 Hz), 2.50-2.65 (m, 8H), 2.30 (s, 3H). $^{13}$C NMR (150 MHz, CDCl$_3$) δ 177.8, 164.0, 161.4, 161.0, 160.8, 160.0, 127.7, 124.1, 115.1, 109.4, 107.8, 96.2, 92.9, 66.3, 57.1, 56.6, 55.9, 55.1, 53.7, 46.1. HRMS (ESI) calcd for $C_{24}H_{29}N_2O_5$ 425.2071 (M+H)$^+$, found 425.2070.

EXAMPLE 11

5,7-Dimethoxy-2-(4-(2-pyrrolidin-1-yl-ethoxy)phenyl)-chromen-4-one (16, HJC-5-57)

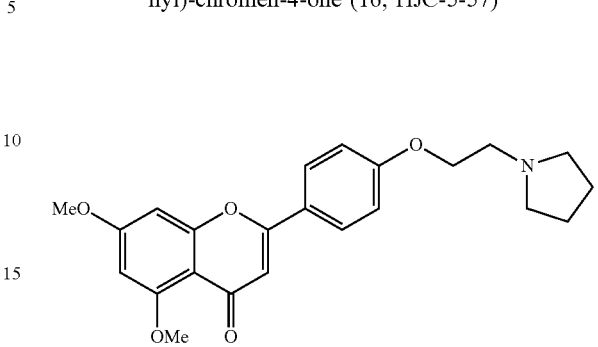

Compound 16 was prepared in 85% yield by a procedure similar to that used to prepare 14. The title compound was obtained as a pale brown solid (mp 114-115° C.). HPLC purity 99.2% ($t_R$=15.91 min). $^1$H NMR (600 MHz, CDCl$_3$) δ 7.78 (d, 2H, J=6.6 Hz), 6.99 (d, 2H, J=6.6 Hz), 6.55 (d, 1H, J=3.6 Hz), 6.52 (d, 1H, J=2.4 Hz), 6.34 (d, 1H, J=2.4 Hz), 4.17 (t, 2H, J=9.0 Hz), 3.92 (s, 3H), 3.88 (s, 3H), 2.93 (t, 2H, J=9.0 Hz), 2.65-2.66 (m, 4H), 1.81-1.82 (m, 4H). $^{13}$C NMR (150 MHz, CDCl$_3$) δ 177.8, 164.0, 161.4, 161.0, 160.8, 160.0, 127.7, 123.9, 115.0, 109.3, 107.7, 96.2, 93.0, 67.3, 56.5, 55.8, 54.9, 54.8, 23.6. HRMS (ESI) calcd for $C_{23}H_{26}NO_5$ 396.1806 (M+H)$^+$, found 396.1809.

EXAMPLE 12

2-(4-(2-Diethylaminoethoxy)-phenyl)-5,7-dimethoxy-chromen-4-one (17, HJC-5-81)

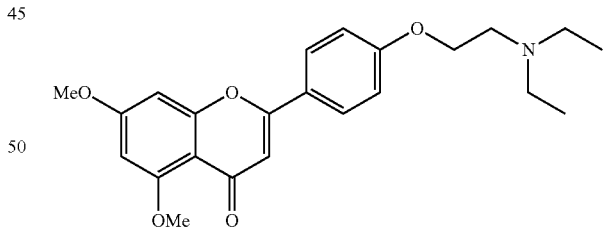

Compound 17 was prepared in 85% yield by a procedure similar to that used to prepare 14. The title compound was obtained as a pale yellow solid (mp 116-117° C.). HPLC purity 99.5% ($t_R$=16.09 min). $^1$H NMR (600 MHz, CDCl$_3$) δ 7.80 (d, 2H, J=9.0 Hz), 7.00 (d, 2H, J=9.0 Hz), 6.59 (d, 1H, J=2.4 Hz), 6.56 (d, 1H, J=1.8 Hz), 6.37 (d, 1H, J=1.8 Hz), 4.12 (t, 2H, J=6.0 Hz), 3.95 (s, 3H), 3.91 (s, 3H), 2.91 (t, 2H, J=6.0 Hz), 2.65-2.68 (m, 4H), 1.09 (t, 6H, J=7.2 Hz). $^{13}$C NMR (150 MHz, CDCl$_3$) δ 177.8, 164.0, 161.5, 161.0, 160.8, 160.0, 127.7, 124.0, 115.1, 109.4, 107.8, 96.2, 93.0, 67.0, 56.6, 55.9, 51.8, 48.0, 12.0. HRMS (ESI) calcd for $C_{23}H_{28}NO_5$ 398.1962 (M+H)$^+$, found 398.1964.

EXAMPLE 13

1-(2-(4-(5,7-Dimethoxy-4-oxo-4H-chromen-2-yl)phenoxy)ethyl)-pyrrolidine-2-carboxylic acid methyl ester (18, HJC-5-80)

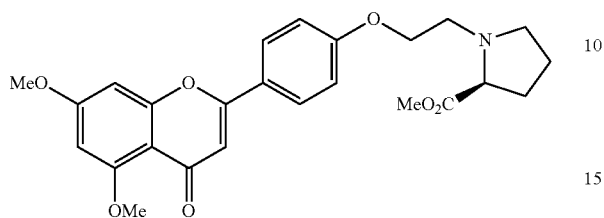

Compound 18 was prepared in 66% yield by a procedure similar to that used to prepare 14. The title compound was obtained as a white solid (mp 121-122° C.). HPLC purity 98.4% ($t_R$=16.15 min). $^1$H NMR (600 MHz, CDCl$_3$) δ 7.83 (d, 2H, J=9.0 Hz), 7.00 (d, 2H, J=9.0 Hz), 6.61 (s, 1H), 6.58 (d, 1H, J=2.4 Hz), 6.40 (d, 1H, J=1.8 Hz), 4.18-4.24 (m, 2H), 3.98 (s, 3H), 3.94 (s, 3H), 3.66 (s, 3H), 3.39-3.41 (m, 1H), 3.32-3.35 (m, 1H), 3.11-3.14 (m, 1H), 3.04-3.07 (m, 1H), 2.59-2.62 (m, 1H), 2.20-2.22 (m, 1H), 1.96-2.00 (m, 2H), 1.86-1.88 (m, 1H). $^{13}$C NMR (150 MHz, CDCl$_3$) δ 177.8, 174.9, 164.0, 161.2, 161.0, 160.8, 160.0, 127.7, 124.1, 115.0, 109.4, 107.9, 96.2, 93.0, 67.5, 66.2, 56.6, 55.9, 55.1, 53.6, 52.0, 29.9, 23.5. HRMS (ESI) calcd for C$_{25}$H$_{28}$NO$_7$ 454.1860 (M+H)$^+$, found 454.1865.

EXAMPLE 14

4.1.15. 5,7-Dimethoxy-2-(4-(piperidin-4-yloxy)-phenyl)-chromen-4-one (19, HJC-5-43)

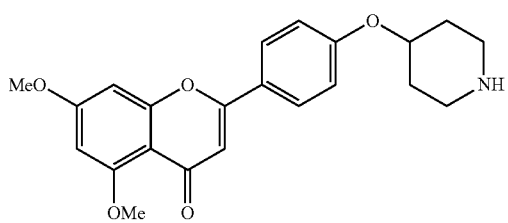 [SMILES: COc1cc(OC)c2c(=O)cc(-c3ccc(OC4CCNCC4)cc3)oc2c1]

To a solution of 6 (60 mg, 0.2 mmol) and Ph$_3$P (210 mg, 0.8 mmol) in THF (5 mL) was added 4-hydroxy-piperidine-1-carboxylic acid tert-butyl ester (121 mg, 0.6 mmol) in THF (5 mL) and DIAD (121 mg, 0.6 mmol). The mixture was stirred at r.t. for 2 h, and was then concentrated to give the crude product. This residue was purified with silica gel column (EtOAc) to afford 80 mg of the intermediate as a white solid. To the solution of the intermediate (80 mg) in CH$_2$Cl$_2$ (3 mL) was added TFA (1 mL) at 0° C. The mixture was stirred at r.t. for 3 h, and was then concentrated. The residue was partitioned between EtOAc (250 mL) and 1 N NaHCO$_3$ (aq., 10 mL). The organic layer was washed with H$_2$O (10 mL) and dried over Na$_2$SO$_4$. The organic layer was concentrated. The residue was purified with silica gel column (EtOAc) to afford 19 (60 mg, 78%, two steps) as a pale yellow solid (mp 205-206° C.). HPLC purity 98.6% ($t_R$=15.43 min). $^1$H NMR (600 MHz, DMSO-d$_6$) δ 7.98-8.00 (m, 2H), 7.15-7.17 (m, 2H), 6.85 (d, 1H, J=1.8 Hz), 6.68 (s, 1H), 6.51 (d, 1H, J=2.4 Hz), 4.77 (t, 1H, J=4.2 Hz), 3.90 (s, 3H), 3.83 (s, 3H), 3.21-3.25 (m, 4H), 3.03-3.07 (m, 2H), 2.09-2.12 (m, 2H), 1.78-1.81 (m, 2H). $^{13}$C NMR (150 MHz, DMSO-d$_6$) δ 178.6, 164.5, 161.3, 160.9, 160.0, 159.4, 128.1, 124.4, 116.1, 108.9, 107.4, 96.4, 93.0, 69.2, 56.3, 55.9, 40.6, 28.0. HRMS (ESI) calcd for C$_{22}$H$_{24}$NO$_5$ 382.1649 (M+H)$^+$, found 382.1651.

EXAMPLE 15

2-(4-(2-Aminoethoxy)-phenyl)-5,7-dimethoxy-chromen-4-one (20, HJC-5-18)

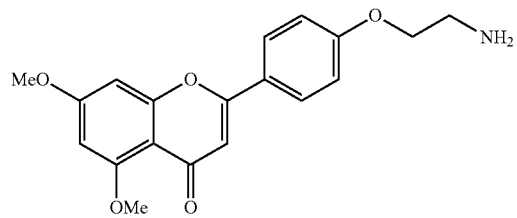 [SMILES: COc1cc(OC)c2c(=O)cc(-c3ccc(OCCN)cc3)oc2c1]

Compound 20 was prepared in 59% yield (two steps) by a procedure similar to that used to prepare 19. The title compound was obtained as a white solid (mp 165-166° C.). HPLC purity 98.4% ($t_R$=14.50 min). $^1$H NMR (600 MHz, CD$_3$OD) δ 7.87 (d, 2H, J=9.0 Hz), 7.05 (d, 2H, J=8.4 Hz), 6.61 (d, 2H, J=9.0 Hz), 6.42 (s, 1H), 4.12 (t, 2H, J=4.8 Hz), 3.94 (d, 6H, J=2.4 Hz), 3.14 (s, 2H). $^{13}$C NMR (150 MHz, CD$_3$OD) δ 178.9, 164.7, 161.7, 161.6, 161.0, 160.1, 128.1, 124.0, 115.1, 108.8, 107.2, 96.5, 93.1, 69.1, 56.2, 56.0, 40.7. HRMS (ESI) calcd for C$_{19}$H$_{20}$NO$_5$ 342.1336 (M+H)$^+$, found 342.1337.

EXAMPLE 16

2-(4-(3-Aminopropoxy)-phenyl)-5,7-dimethoxy-chromen-4-one (21, HJC-5-42)

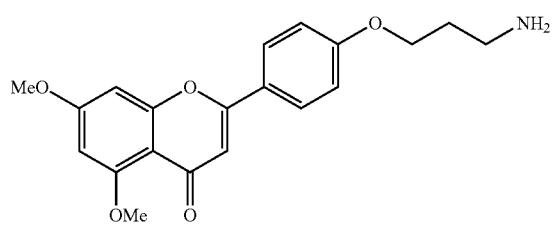 [SMILES: COc1cc(OC)c2c(=O)cc(-c3ccc(OCCCN)cc3)oc2c1]

Compound 21 was prepared in 90% yield (two steps) by a procedure similar to that used to prepare 19. The title compound was obtained as a white solid (mp 170-171° C.). HPLC purity 98.4% ($t_R$=15.07 min). $^1$H NMR (600 MHz, CD$_3$OD) δ 7.88 (d, 2H, J=9.0 Hz), 7.05 (d, 2H, J=9.0 Hz), 6.66 (d, 1H, J=1.8 Hz), 6.60 (s, 1H), 6.45 (d, 1H, J=1.8 Hz), 4.18 (t, 2H, J=6.0 Hz), 3.95 (d, 6H, J=3.0 Hz), 3.35 (s, 2H), 3.09 (t, 2H, J=7.2 Hz), 2.14 (t, 2H, J=6.0 Hz). $^{13}$C NMR (150 MHz, CD$_3$OD) δ 179.3, 165.2, 162.2, 161.9, 161.1, 160.4, 128.3, 124.1, 115.3, 108.9, 107.1, 96.8, 93.4, 65.9, 56.3, 56.2, 38.2, 29.4. HRMS (ESI) calcd for C$_{20}$H$_{22}$NO$_5$ 356.1493 (M+H)$^+$, found 356.1496.

EXAMPLE 17

5,7-Dimethoxy-2-(4-oxiranylmethoxyphenyl)-chromen-4-one (23, HJC-5-61)

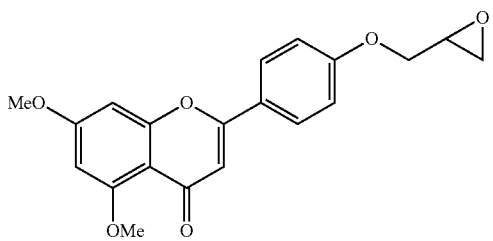 [SMILES: COc1cc(OC)c2c(=O)cc(-c3ccc(OCC4CO4)cc3)oc2c1]

To a solution of 6 (200 mg, 0.67 mmol) and epichlorohydrin (22) (617 mg, 6.7 mmol) in acetone (10 mL) was added $K_2CO_3$ (462 mg, 3.35 mmol). The mixture was stirred at 80° C. for 24 h, and was then concentrated to give the crude product. The residue was diluted with EtOAc (100 mL), and washed with 0.1 N HCl (aq.) (10 mL) followed by brine (10 mL). The organic layer was dried over anhydrous $Na_2SO_4$, and then concentrated under reduced pressure. The residue was purified by silica gel column chromatography ($CH_2Cl_2$/MeOH=20/1) to give the desired product 23 (160 mg, 67%) as a pale yellow solid (mp 191-192° C.). HPLC purity 98.9% ($t_R$=18.99 min). $^1$H NMR (600 MHz, CDCl$_3$) δ 7.80-7.82 (m, 2H), 7.00-7.03 (m, 2H), 6.58 (s, 1H), 6.55 (d, 1H, J=2.4 Hz), 6.36 (d, 1H, J=2.4 Hz), 4.31-4.33 (m, 1H), 3.99-4.02 (m, 1H), 3.95 (s, 3H), 3.90 (s, 3H), 3.37-3.39 (m, 1H), 2.93-2.94 (m, 1H), 2.78-2.79 (m, 1H). $^{13}$C NMR (150 MHz, CDCl$_3$) δ 177.7, 164.1, 161.0, 161.0, 160.6, 160.0, 127.8, 124.6, 115.1, 109.4, 108.0, 96.2, 93.0, 69.1, 56.6, 55.9, 50.1, 44.7. HRMS (ESI) calcd for $C_{20}H_{19}O_6$ 355.1176 (M+H)$^+$, found 355.1180.

EXAMPLE 18

2-(4-(2-Hydroxy-3-piperidin-1-yl-propoxy)phenyl)-5,7-dimethoxy-chromen-4-one (24, HJC-5-100)

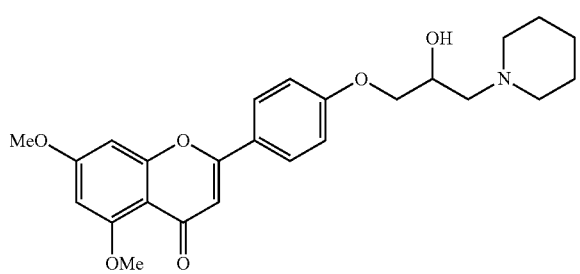 [SMILES: COc1cc(OC)c2c(=O)cc(-c3ccc(OCC(O)CN4CCCCC4)cc3)oc2c1]

To a solution of 23 (30 mg, 0.085 mmol) and piperidine (72 mg, 0.85 mmol) in EtOH (5 mL) was added $K_2CO_3$ (117 mg, 0.85 mmol). The mixture was stirred at 100° C. for 3 h, and was then concentrated to give the crude product. The residue was diluted with EtOAc (100 mL), and washed with 0.1 N HCl (aq.) (10 mL) followed by brine (10 mL). The organic layer was dried over anhydrous $Na_2SO_4$, and then concentrated under reduced pressure. The residue was purified by silica gel column chromatography ($CH_2Cl_2$/MeOH=10/1) to give the desired product 24 (35 mg, 94%) as a white solid (mp 109-110° C.). HPLC purity 98.5% ($t_R$=15.78 min). $^1$H NMR (600 MHz, CDCl$_3$) δ 7.79-7.81 (m, 2H), 7.00-7.03 (m, 2H), 6.58 (s, 1H), 6.54 (d, 1H, J=3.0 Hz), 6.36 (d, 1H, J=1.8 Hz), 4.11-4.15 (m, 1H), 4.02-4.06 (m, 2H), 3.95 (s, 3H), 3.90 (s, 3H), 2.66 (bs, 1H), 2.54-2.56 (m, 2H), 2.50-2.55 (m, 2H), 2.41-2.43 (m, 2H), 1.58-1.65 (m, 4H), 1.46-1.48 (m, 2H). $^{13}$C NMR (150 MHz, CDCl$_3$) δ 177.8, 164.0, 161.4, 161.0, 160.8, 160.0, 127.7, 124.2, 115.1, 109.3, 107.8, 96.2, 92.9, 70.7, 65.3, 61.1, 56.6, 55.9, 54.9, 26.0, 24.2. HRMS (ESI) calcd for $C_{25}H_{30}NO_6$ 440.2068 (M+H)$^+$, found 440.2071.

EXAMPLE 19

2-(4-(2-Hydroxy-3-pyrrolidin-1-yl-propoxy)phenyl)-5,7-dimethoxy-chromen-4-one (25, HJC-6-4)

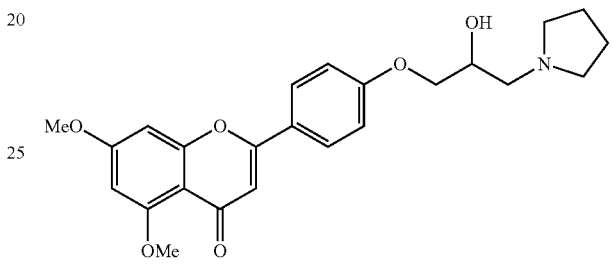

25 was prepared in 94% yield by a procedure similar to that used to prepare 24. The title compound was obtained as a pale yellow solid (mp 137-138° C.). HPLC purity 99.9% ($t_R$=15.42 min). $^1$H NMR (600 MHz, CDCl$_3$) δ 7.82 (d, 2H, J=9.0 Hz), 7.03 (d, 2H, J=9.0 Hz), 6.59 (s, 1H), 6.55 (d, 1H, J=2.4 Hz), 6.36 (d, 1H, J=2.4 Hz), 4.12-4.15 (m, 1H), 4.06 (d, 2H, J=5.4 Hz), 3.95 (s, 3H), 3.91 (s, 3H), 3.10-3.30 (bs, 1H), 2.86-2.89 (m, 1H), 2.76-2.79 (m, 2H), 2.58-2.62 (m, 2H), 1.82-1.85 (m, 4H). $^{13}$C NMR (150 MHz, CDCl$_3$) δ 177.8, 164.1, 161.3, 161.0, 160.7, 160.0, 127.7, 124.3, 115.1, 109.4, 107.9, 96.2, 93.0, 70.7, 67.2, 58.6, 56.6, 55.9, 54.4. HRMS (ESI) calcd for $C_{24}H_{28}NO_6$ 426.1911 (M+H)$^+$, found 426.1915.

EXAMPLE 20

2-(4-(3-Dimethylamino-2-hydroxypropoxy)-phenyl)-5,7-dimethoxy-chromen-4-one (26, HJC-5-65)

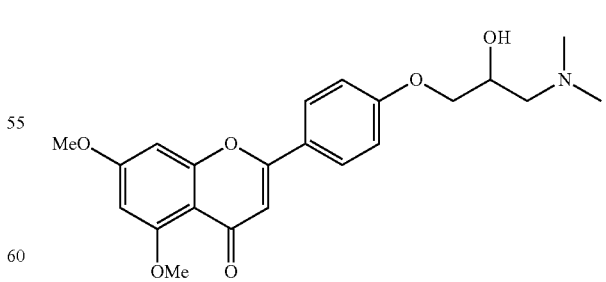

26 was prepared in 71% yield by a procedure similar to that used to prepare 24. The title compound was obtained as a white solid (mp 92-93° C.). HPLC purity 99.6% ($t_R$=10.65 min). $^1$H NMR (600 MHz, CDCl$_3$) δ 7.83 (d, 2H, J=9.0 Hz), 7.04 (d, 2H, J=9.0 Hz), 6.61 (s, 1H), 6.58 (d, 1H, J=2.4 Hz), 6.39 (d, 1H, J=2.4 Hz), 4.12-4.15 (m, 1H), 4.11-4.12 (m, 2H), 3.98 (s, 3H), 3.93 (s, 3H), 2.61-2.65 (m, 1H), 2.42-2.48 (m, 2H), 2.39 (s, 6H). $^{13}$C NMR (150 MHz, CDCl$_3$) δ 177.8, 164.1, 161.3, 161.0, 160.8, 160.0, 127.7, 124.2, 115.1, 109.3, 107.9, 96.2, 93.0, 70.7, 66.1, 61.8, 56.6, 55.9, 45.6. HRMS (ESI) calcd for C$_{22}$H$_{26}$NO$_6$ 400.1755 (M+H)$^+$, found 400.1756.

EXAMPLE 21

2-(4-(2,3-Dihydroxypropoxy)phenyl)-5,7-dimethoxy-chromen-4-one (28, HJC-5-99)

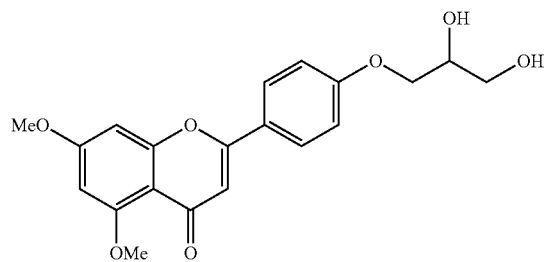 [SMILES: COc1cc(OC)c2c(=O)cc(-c3ccc(OCC(O)CO)cc3)oc2c1]

To a solution of 6 (50 mg, 0.17 mmol) and Ph$_3$P (88 mg, 0.34 mmol) in THF (5 mL) was added (2,2-dimethyl-1,3-dioxolan-4-yl)methanol (27) (44 mg, 0.34 mmol) in THF (5 mL) and DIAD (68 mg, 0.34 mmol). The mixture was stirred at r.t. for 4 h, and was then concentrated to give the crude product. This residue was purified with silica gel column (CH$_2$Cl$_2$/MeOH=20/1 to 10/1) to afford 70 mg of the intermediate as a white solid. To the solution of the intermediate (70 mg) in EtOH (5 mL) was added 0.5 N HCl (aq., 0.5 mL) at 0° C. The mixture was stirred at 100° C. for 2 h, and was then concentrated. The residue was partitioned between EtOAc (50 mL) and 1 N NaHCO$_3$ (aq., 10 mL). The organic layer was washed with H$_2$O (10 mL) and dried over Na$_2$SO$_4$. The organic layer was concentrated. The residue was purified with silica gel column (CH$_2$Cl$_2$/MeOH=10/1) to afford 28 (45 mg, 71%, two steps) as a white solid (mp 203-204° C.). HPLC purity 97.6% (t$_R$=15.51 min). $^1$H NMR (600 MHz, DMSO-d$_6$) δ 7.97-8.00 (m, 2H), 7.08-7.11 (m, 2H), 6.86 (d, 1H, J=2.4 Hz), 6.66 (s, 1H), 6.50 (d, 1H, J=2.4 Hz), 5.00 (d, 1H, J=5.4 Hz), 4.70 (t, 1H, J=6.0 Hz), 4.09-4.11 (m, 1H), 3.95-3.98 (m, 1H), 3.90 (s, 3H), 3.83 (s, 3H), 3.80-3.83 (m, 1H), 3.46 (t, 2H, J=6.0 Hz). $^{13}$C NMR (150 MHz, DMSO-d$_6$) δ 175.6, 163.6, 161.4, 160.2, 159.7, 159.1, 127.7, 122.9, 115.0, 108.3, 106.7, 96.2, 93.4, 69.9, 69.8, 62.6, 56.1, 56.0. HRMS (ESI) calcd for C$_{20}$H$_{21}$O$_7$ 373.1282 (M+H)$^+$, found 373.1284.

EXAMPLE 22

2-(4-Bromophenyl)-5,7-dimethoxy-chromen-4-one (31, HJC-5-78)

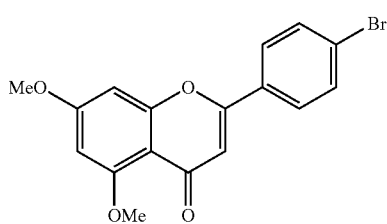 [SMILES: COc1cc(OC)c2c(=O)cc(-c3ccc(Br)cc3)oc2c1]

Starting from the commercially available 4-bromobenzaldehyde (29) and 1-(2-hydroxy-4,6-dimethoxy-phenyl)ethanone (2), 31 was prepared in two steps according to literature procedures.$^{36}$ HPLC purity 96.5% (t$_R$=21.53 min). $^1$H NMR (600 MHz, DMSO-d$_6$) δ 7.99 (d, 2H, J=8.4 Hz), 7.75 (d, 2H, J=9.0 Hz), 6.87 (d, 1H, J=2.4 Hz), 6.82 (s, 1H), 6.51 (d, 1H, J=1.8 Hz), 3.90 (s, 3H), 3.83 (s, 3H). $^{13}$C NMR (150 MHz, DMSO-d$_6$) δ 175.6, 163.9, 160.3, 159.1, 158.5, 132.0, 130.2, 127.9, 125.1, 108.6, 108.4, 96.4, 93.4, 56.1, 56.0. HRMS (ESI) calcd for C$_{17}$H$_{14}$BrO$_4$ 361.0070 (M+H)$^+$, found 361.0070.

EXAMPLE 23

2-(4-(6-Fluoropyridin-3-yl)phenyl)-5,7-dimethoxy-chromen-4-one (33, HJC-6-7)

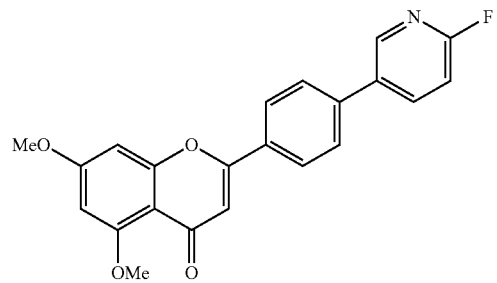 [SMILES: COc1cc(OC)c2c(=O)cc(-c3ccc(-c4ccc(F)nc4)cc3)oc2c1]

To a solution of 31 (90 mg, 0.25 mmol) and 2-fluoropyridine-5-boronic acid (32) (42 mg, 0.3 mmol) in THF/EtOH/H$_2$O (2 mL/2 mL/2 mL) was added KOAc (94 mg, 0.75 mmol) and then Pd(dppf)Cl$_2$ (20 mg, 0.025 mmol). The resulting mixture was deoxygenated via five vacuum/N$_2$-refill cycles. The mixture was stirred at 80° C. for 18 h, and was then concentrated under vacuum. The residue was partitioned between EtOAc (100 mL) and H$_2$O (20 mL). The organic layer was separated and washed with brine (10 mL), dried over anhydrous Na$_2$SO$_4$, filtrated and concentrated to give an oily residue. This residue was purified with silica gel column (CH$_2$Cl$_2$/MeOH=10/1) to obtain 33 (80 mg, 85%) as a pale red solid (mp 209-210° C.). HPLC purity 98.4% (t$_R$=20.91 min). $^1$H NMR (600 MHz, CDCl$_3$) δ 8.48 (d, 1H, J=1.8 Hz), 8.01-8.04 (m, 1H), 7.98 (s, 1H), 7.97 (s, 1H), 7.04-7.06 (m, 1H), 6.72 (s, 1H), 6.59 (d, 1H, J=2.4 Hz), 6.40 (d, 1H, J=2.4 Hz), 3.97 (s, 3H), 3.93 (s, 3H). $^{13}$C NMR (150 MHz, CDCl$_3$) δ 177.5, 164.5, 164.4, 162.9, 161.2, 160.1, 160.0, 146.2, 146.1, 139.8, 139.5, 133.8, 131.6, 127.6, 126.9, 110.0, 109.8, 109.6, 96.5, 93.1, 56.6, 55.9. HRMS (ESI) calcd for C$_{22}$H$_{17}$FNO$_4$ 378.1136 (M+H)$^+$, found 378.1138.

EXAMPLE 24

2-(4-(2-Dimethylaminoethylamino)phenyl)-5,7-dimethoxy-chromen-4-one (36, HJC-6-11)

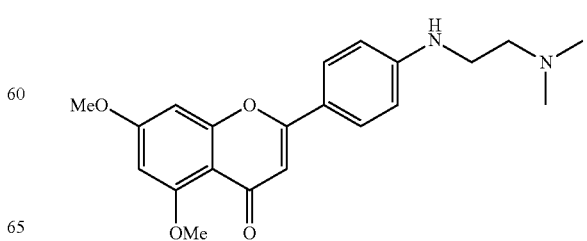

NaO'Bu (43 mg, 0.45 mmol), Pd$_2$(dba)$_3$ (28 mg, 0.03 mmol) and (±)-BINAP (19 mg, 0.03 mmol) were placed into a flask and dissolved into distilled toluene (10 mL). To this solution was added 31 (108 mg, 0.3 mmol) and N,N-dimethylethylenediamine (34) (40 mg, 0.45 mmol) dropwise with stirring at room temperature and the mixture was refluxed at 80° C. for 48 h. After the mixture was cooled, 20 mL of H$_2$O was added and extracted with EtOAc (100 mL). The organic layer was dried over anhydrous Na$_2$SO$_4$, filtered and concentrated in vacuo. The residue was purified by silica gel column chromatography (CH$_2$Cl$_2$/MeOH=10/1) to give the desired product (65 mg, 64%) as a pale yellow solid (mp 159-160° C.). HPLC purity 98.8% ($t_R$=15.10 min). $^1$H NMR (600 MHz, CDCl$_3$) δ 7.70 (d, 2H, J=9.0 Hz), 6.66 (d, 2H, J=9.0 Hz), 6.54 (d, 1H, J=1.8 Hz), 6.53 (s, 1H), 6.35 (d, 1H, J=1.8 Hz), 4.84 (s, 1H), 3.95 (s, 3H), 3.90 (s, 3H), 3.22 (s, 2H), 2.60 (t, 1H, J=6.0 Hz), 2.28 (s, 6H). $^{13}$C NMR (150 MHz, CDCl$_3$) δ 177.9, 163.8, 161.7, 161.0, 160.0, 151.1, 127.7, 119.4, 112.5, 109.4, 106.2, 96.0, 93.0, 57.7, 56.6, 55.8, 45.2, 40.6, 31.1. HRMS (ESI) calcd for C$_{21}$H$_{25}$N$_2$O$_4$ 369.1809 (M+H)$^+$, found 369.1811.

EXAMPLE 25

5,7-Dimethoxy-2-(4-(2-pyrrolidin-1-yl-ethylamino-phenyl)-phenyl)-chromen-4-one (37, HJC-6-23)

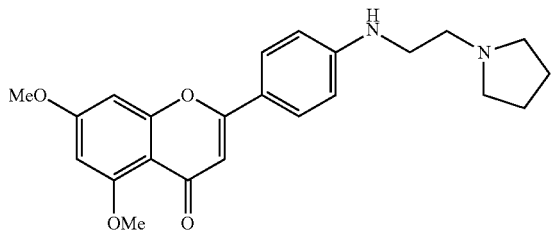 [SMILES: COc1cc(OC)c2c(=O)cc(-c3ccc(NCCN4CCCC4)cc3)oc2c1]

37 was prepared in 57% yield by a procedure similar to that used to prepare 36. The title compound was obtained as a pale yellow solid (mp 148-149° C.). HPLC purity 98.2% ($t_R$=15.73 min). $^1$H NMR (600 MHz, CDCl$_3$) δ 7.69 (d, 2H, J=9.0 Hz), 6.66 (d, 2H, J=8.4 Hz), 6.53 (d, 1H, J=2.4 Hz), 6.52 (s, 1H), 6.34 (d, 1H, J=2.4 Hz), 4.91 (s, 1H), 3.94 (s, 3H), 3.89 (s, 3H), 3.27 (d, 2H, J=2.4 Hz), 2.78 (t, 1H, J=6.0 Hz), 2.59 (s, 4H), 1.81 (s, 4H). $^{13}$C NMR (150 MHz, CDCl$_3$) δ 177.9, 163.8, 161.7, 161.0, 160.0, 151.1, 127.6, 119.3, 112.5, 109.4, 106.1, 96.0, 93.0, 56.5, 55.8, 54.6, 54.0, 41.8, 23.6. HRMS (ESI) calcd for C$_{23}$H$_{27}$N$_2$O$_4$ 395.1965 (M+H)$^+$, found 395.1968.

EXAMPLE 26

5-Hydroxy-7-methoxy-2-(4-(2-pyrrolidin-1-yl-ethoxyphenyl)-chromen-4-one (38, HJC-5-97)

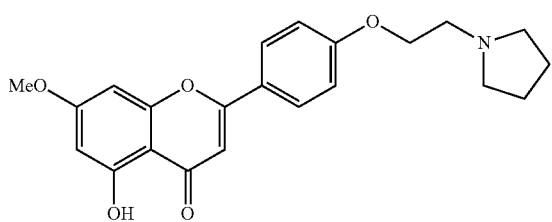 [SMILES: COc1cc(O)c2c(=O)cc(-c3ccc(OCCN4CCCC4)cc3)oc2c1]

To a solution of 16 (30 mg, 0.076 mmol) in 5 mL of CH$_2$Cl$_2$ was added 1 N BBr$_3$ in CH$_2$Cl$_2$ (0.15 mL, 0.15 mmol) at 0° C. The resulting mixture was stirred at r.t. for 2 h. The solution was diluted with CH$_2$Cl$_2$/MeOH (10/1, 50 mL), washed with H$_2$O (15 mL) and brine (10 mL). The organic layer was dried over anhydrous Na$_2$SO$_4$ and then concentrated under reduced pressure. The residue was purified by silica gel column chromatography (CH$_2$Cl$_2$/MeOH=10/1) to give the desired product (23 mg, 79%) as a pale yellow solid (mp 127-129° C.). HPLC purity 99.7% ($t_R$=18.02 min). $^1$H NMR (600 MHz, CDCl$_3$) δ 12.81 (s, 1H), 7.83 (d, 2H, J=9.0 Hz), 7.03 (d, 2H, J=9.0 Hz), 6.60 (s, 1H), 6.48 (d, 1H, J=2.4 Hz), 6.36 (d, 1H, J=2.4 Hz), 4.21 (t, 2H, J=9.0 Hz), 3.88 (s, 3H), 2.97 (t, 2H, J=9.0 Hz), 2.67-2.69 (m, 4H), 1.83-1.85 (m, 4H). $^{13}$C NMR (150 MHz, CDCl$_3$) δ 182.6, 165.6, 164.2, 162.3, 162.0, 157.9, 128.2, 123.8, 115.2, 105.7, 104.5, 98.2, 92.8, 67.4, 55.9, 54.9, 54.8, 23.6. HRMS (ESI) calcd for C$_{22}$H$_{24}$NO$_5$ 382.1649 (M+H)$^+$, found 386.1652.

EXAMPLE 27

5,7-Dihydroxy-2-(4-(2-pyrrolidin-1-yl-ethoxy)phenyl-chromen-4-one (39, HJC-6-1)

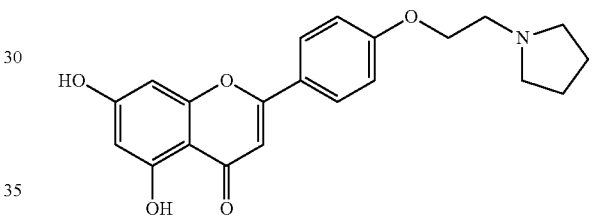

To a solution of 16 (22 mg, 0.056 mmol) in 5 mL of CH$_2$Cl$_2$ was added 1 N BBr$_3$ in CH$_2$Cl$_2$ (0.17 mL, 0.17 mmol) at 0° C. The resulting mixture was stirred at r.t. for 24 h. The solution was diluted with CH$_2$Cl$_2$/MeOH (10/1, 50 mL), washed with H$_2$O (5 mL) and brine (5 mL). The organic layer was dried over anhydrous Na$_2$SO$_4$ and then concentrated under reduced pressure. The residue was purified by silica gel column chromatography (CH$_2$Cl$_2$/MeOH=10/1) to give the desired product (15 mg, 73%) as a pale yellow solid (mp 228-229° C.). HPLC purity 97.5% ($t_R$=16.04 min). $^1$H NMR (600 MHz, CDCl$_3$/CD$_3$OD 2:1) δ 7.80 (d, 2H, J=9.0 Hz), 6.98 (d, 2H, J=9.0 Hz), 6.50 (s, 1H), 6.39 (d, 1H, J=2.4 Hz), 6.22 (d, 1H, J=2.4 Hz), 4.16 (t, 2H, J=6.0 Hz), 2.94 (t, 2H, J=6.0 Hz), 2.65-2.67 (m, 4H), 1.80-1.83 (m, 4H). $^{13}$C NMR (150 MHz, CDCl$_3$/CD$_3$OD 2:1) δ 182.6, 164.4, 164.3, 161.8, 161.7, 158.1, 128.2, 123.8, 115.1, 104.7, 103.9, 99.4, 94.5, 66.8, 54.8, 54.7, 23.4. HRMS (ESI) calcd for C$_{21}$H$_{22}$NO$_5$ 368.1493 (M+H)$^+$, found 368.1495.

EXAMPLE 28

Biological Characterization of Apigenin Analogues

Human Pancreatic Stellate Cell Culture and Reagents.

Under an IRB-approved tissue protocol, discarded human resected pancreatic tissue (500 mm$^3$) was attained fresh from the operating room at the University of Texas Medical Branch. The tissue was minced and plated on a collagen-coated flask (15 µg/mL, Invitrogen) with DMEM (VWR;

Radnor, Pa.) supplemented with penicillin 200 U/mL, streptomycin 200 µg/mL, amphotericin B 0.25 µg/mL and gentimicin 50 µg/mL (Invitrogen, Carlsbad Calif.), 10% fetal bovine serum (Lonza, Walkersville, Md.), 1% insulin-transferrin, selenium-ethanolamine (Gibco, Grand Island, N.Y.), and 1% non-essential amino acids (Sigma-Aldrich, St. Louis, Mo.). The human PSC were isolated by the outgrowth method.[41-43] The purity of PSC culture was confirmed by immunohistochemical staining for vimentin, α-smooth muscle actin, glial fibrillar acidic protein, or Oil red O staining. Primary PSC were transformed and immortalized for use in experiments using lentiviral vectors containing SV40 Large T antigen and human telomerase (plasmid #12245 and 12246; Addgene, Cambridge, Mass.). Cultures were maintained in DMEM with 10% FBS, at 37° C. in a humidified 95% $O_2$/5% $CO_2$ atmosphere.

Cell proliferation assay. Transformed PSC ($3\times10^3$) were plated in 96-well plates, in sextuplicate. The next day, the media was changed to 1% FBS with apigenin or analogues for 24-48 h. AlamarBlue reagent (10% sample volume, DAL1025) was added to each well per Invitrogen's protocol. Fluorescence was recorded using excitation/emission wavelengths of 544/590 nm and the SpectraMax M2 Microplate Reader (Molecular Devices, Sunnyvale Calif.).

Cell death assay. Transformed PSC ($8\times10^3$) were plated in 96-well plates in triplicate. The next day, the media was changed to 1% FBS with apigenin or analogues for a 14 h incubation. The Cell Death Detection ELISA$^{PLUS}$ assay (Roche Applied Science, Indianapolis, Ind.) was used and protocol followed (Version 11.0). Absorbance was measured at 405 nm, using the EL×800 Automated Microplate Reader (Bio-TEK Instruments, Inc., Winooski, Vt.).

Chronic pancreatitis (CP) animal model. Animal experiments were conducted under an Institutional Animal Care and Use Committee-approved protocol. CP was induced in C57BL/6 mice using supraoptimal pancreatic stimulation with cerulein (CR), a cholecystokinin analogue (Bachem, Torrance, Calif.). CP (50 µg CR/kg mouse weight) was administered via intraperitoneal route hourly for 5 h for 3 d/week for a total of 4 weeks. Control mice received phosphate buffered saline (PBS) injections following the same schedule. Starting Week 2 of the experiment, apigenin, analogue, or vehicle (0.5% methylcellulose+0.025% Tween 20 in dd$H_2$O) were administered (0.5 mg/kg/d, oral gavage, once daily, 6 d/week, for 3 week) while continuing CR injections. At the end of Week 4, the mice were anesthestized with isoflurane and sacrificed per protocol. The pancreata were quickly harvested and processed.

Immunohistochemistry (IHC) and image analysis. Pancreata were formalin-fixed and paraffin-embedded. Prior to staining, sections (5 µm) were deparaffinized with xylene, dehydrated with ethanol, and subjected to heat-mediated antigen retrieval (DAKO, Carpinteria, Calif.) to optimize antigen immunoreactivity. Fibronectin antibody (1:600; Santa Cruz Biotechnology, Dallas, Tex.), and biotinylated anti-goat IgG (1:400; Vector Laboratories Inc., Burlingame, Calif.) were used. IHC staining was completed with the VECTASTAIN Elite ABC kit (Vector Lab), color development with DAB (DAKO), and counterstaining with hematoxylin 7211 (Thermo Scientific, Kalamazoo, Mich.). Five non-overlapping images of each pancreas (400×) were taken using an Olympus BX51 microscope connected to a DP71 Olympus digital camera. The percent area of brown fibronectin staining was quantified using the Image Processing and Analysis in Java (ImageJ) 1.46r software (NIH, Bethesda, Md.) and a color deconvolution plug-in (Ruifrok and Johnston, *Anal Quant Cytol Histol* 2001, 23:291; Schneider et al., *Nat Methods* 2012, 9:671).

Statistical analysis. Dose-response curves were generated by plotting fluorescence or absorbance versus log (compound concentration). A best-fit curve was created using nonlinear regression, and the $IC_{50}$ or $EC_{50}$ determined from the graph (GraphPad Prism 5; GraphPad Software Inc., La Jolla, Calif.). To analyze continuos variables, unpaired student t-tests and one-way ANOVA with Tukey-Kramer multiple comparisons post-test (GraphPad Prism 5). Significance was set at $p<0.05$.

Recombinant human CBS protein expression and purification. The expression and purification of human CBS was performed as described previously (Asimakopoulou et al. 2013, *Br J Pharmacol.* 169(4):922-32). Briefly, *E. Coli* BL21(DE3) Codon Plus cells (Stratagene, La Jolla, Calif., USA) containing the expression vector pGEX-Kg/GST-CBS were grown at 37° C. and 180 rpm in LuriaBertani (LB) broth medium containing 100 µg/ml ampicillin to an absorption of 0.6-0.8 at 600 nm. Protein expression was induced by addition of 0.1 mM IPTG (isopropyl-b-D-thiogalactopyranoside) and cells were further incubated at 30° C. overnight. The bacteria were harvested and sonicated in lysis buffer PBS (140 mM NaCl, 2.7 mM KCl, 10 mM $Na_2HPO_4$, 1.8 mM $KH_2PO_4$, pH 7.8) containing a protease inhibitors cocktail (Sigma). The protein lysate was loaded onto a GSTrap FF 1 ml affinity column (Amersham Biosciences) and the GST-CBS recombinant protein was eluted with the elution buffer (50 mM Tris-HCl, 10 mM reduced glutathione, pH 8.0) and then dialyzed and concentrated in 10 mM sodium phosphate buffer (pH 8.2) and DTT (1 mM).

Measurement of $H_2S$ production by recombinant CBS. The measurement of $H_2S$ production by recombinant CBS enzyme was performed as described (Asimakopoulou et al. 2013, *Br J Pharmacol.* 169(4):922-32). Briefly, each test consisted of a 100 µl reaction mixture in 50 mM sodium phosphate buffer pH 8.2 containing 1 µg of the purified human CBS enzyme, 0.01 mM pyridoxal-5'-phosphate (PLP), 10 mM L-cysteine and 0.5 mM homocysteine. Apigenin or its various analogs (100 µM) was added to the reaction 15 min before the addition of L-cysteine/homocysteine to the solution. The reaction was initiated by transferring the Eppendorf tubes from ice to a 37° C. shaking water bath. After 60 minutes of incubation at 37° C., the reaction was terminated by adding 1% ZnAc followed by 10% trichloroacetic acid. Subsequently, N,N-dimethylphenylendiamine sulfate (20 mM in 7.2 M HCl) and $FeCl_3$ (30 mM in 1.2 M HCl) were added and the optical absorbance of the solutions was measured at 650 nm. All samples were assayed in triplicate and the effect of the various test compounds on $H_2S$ production was expressed as % of control (in the absence of apigenin or its analogs), which was considered 100%.

TABLE 2

Cystathionine-β-synthase (CBS) inhibitory effects of apigenin and its new analogues.

| Name | CBS Activity % |
| --- | --- |
| Apigenin 100 µM | 80.766 |
| HJC 0392 | 109.674 |
| HJC 0402 | 113.494 |
| HJC 0404 | 116.546 |
| HJC 0407 | 110.027 |
| HJC 0408 | 119.909 |

TABLE 2-continued

Cystathionine-β-synthase (CBS) inhibitory effects of apigenin and its new analogues.

| Name | CBS Activity % |
|---|---|
| HJC 0511 | 113.556 |
| HJC 0513 | 112.477 |
| HJC 0514 | 129.936 |
| HJC 0515 | 125.099 |
| HJC 0516 | 116.982 |
| HJC 0518 | 118.622 |
| HJC 0538 | 122.462 |
| HJC 0542 | 115.57 |
| HJC 0543 | 115.072 |
| HJC 0551 | 120.531 |
| HJC 0553 | 124.206 |
| HJC 0554 | 126.656 |
| HJC 0556 | 128.524 |
| HJC 0557 | 130.538 |
| HJC 0561 | 119.39 |
| HJC 0565 | 116.919 |
| HJC 0574 | 83.932 |
| HJC 0576 | 108.428 |
| HJC 0578 | 69.442 |
| HJC 0580 | 115.84 |
| HJC 0581 | 105.584 |
| HJC 0597 | 109.072 |
| HJC 0599 | 104.069 |
| HJC 05100 | 78.97 |
| HJC 0601 | 99.585 |
| HJC 0604 | 85.946 |
| HJC 0607 | 107.141 |
| HJC 0611 | 112.207 |
| HJC 0623 | 108.823 |

The invention claimed is:

1. Certain embodiments are directed to compounds having the general formula of Formula II:

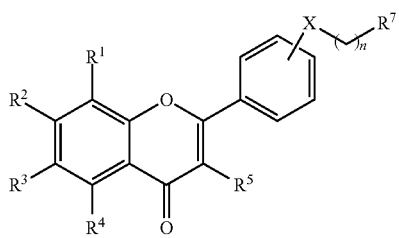

Formula II where X is O;
n is 1, 2, 3, 4, or 5;
$R^1$, $R^3$, and $R^5$ are hydrogen;
$R^2$ and $R^4$ are methoxy; and
$R^7$ is a C1-C6 hydroxyalkyl substituted by a 3 to 8 membered heterocycle, or a 3 to 8 membered heterocycle.

2. The compound of claim 1, wherein X is at the 4' position.

3. The compound of claim 1, wherein n is 2.

4. The compound of claim 1, wherein $R^7$ is a 3 or 6 member heterocycle.

5. The compound of claim 4 wherein $R^7$ is an epoxide.

6. The compound of claim 1, wherein the compound is selected from 5,7-Dimethoxy-2-[4-(2-morpholin-4-yl-ethoxy)-phenyl]-chromen-4-one (HJC-5-16), 5,7-Dimethoxy-2-[4-(2-piperidin-1-yl-ethoxy)-phenyl]-chromen-4-one (HJC-5-56), 5,7-Dimethoxy-2-[4-(2-pyrrolidin-1-yl-ethoxy)-phenyl]-chromen-4-one (HJC-5-57), 5,7-Dimethoxy-2-[4-(piperidin-4-yloxy)-phenyl]-chromen-4-one (HJC-5-43), 5,7-Dimethoxy-2-(4-oxiranylmethoxy-phenyl)-chromen-4-one (HJC-5-61), 2-[4-(2-Hydroxy-3-piperidin-1-yl-propoxy)-phenyl]-5,7-dimethoxy-chromen-4-one (HJC-5-100), or 2-[4-(2-Hydroxy-3-pyrrolidin-1-yl-propoxy)-phenyl]-5,7-dimethoxy-chromen-4-one (HJC-6-4).

* * * * *